United States Patent [19]
Peake et al.

[11] Patent Number: 5,081,287
[45] Date of Patent: Jan. 14, 1992

[54] PESTICIDAL POLYHALO ALKENOIC ACID ESTERS

[75] Inventors: Clinton J. Peake, Trenton; Thomas G. Cullen, Milltown; Anthony J. Martinez, Hamilton Square, all of N.J.

[73] Assignee: FMC Corporation, Philadelphia, Pa.

[21] Appl. No.: 373,423

[22] Filed: Jun. 30, 1989

[51] Int. Cl.$^5$ .................. C07C 69/52; C07C 69/73
[52] U.S. Cl. .................. 560/219; 560/223; 560/225; 560/226; 560/227; 560/229
[58] Field of Search ............... 560/219, 223, 226, 227, 560/225, 229

[56] References Cited

U.S. PATENT DOCUMENTS

| | | | |
|---|---|---|---|
| 3,080,405 | 3/1963 | Larsen et al. | 560/223 |
| 4,603,147 | 7/1986 | Peake et al. | 514/743 |

*Primary Examiner*—Alan L. Rotman
*Attorney, Agent, or Firm*—Norman L. Craig; Robert M. Kennedy; Robert L. Andersen

[57] ABSTRACT

The present invention discloses and exemplifies alcohol, ether and ester derivatives of difluoroalkanes and difluoroalkenylalkanes having the general formula $R-(CH_2)_m-CR^2R^3-OR^1$, in which R is a 1,1-difluoroalkyl or a 1,1-difluoroalkenyl group, composition thereof, and use thereof to control agricultural crop pests.

9 Claims, No Drawings

PESTICIDAL POLYHALO ALKENOIC ACID ESTERS

The present invention relates to certain alcohol, ether and ester derivatives of difluoroalkanes or difluoroalkenylalkanes, formulated compositions thereof, and their use as pesticides to control pests, such as insects, acarids, and nematodes, that prey on agricultural crops.

The compounds of this invention are difluoroalkane or difluoroalkenylalkane derivatives of structural formula I, $R-(CH_2)_m-CR^2R^3-OR^1$.

In formula I, R is a 1,1-difluoroalkyl group of 1 to 4 carbon atoms or a 1,1-difluoroalkenyl group of 2 to 4 carbon atoms, optionally carrying one to four additional halogen substituents. The R group may be, for example, $F_2XC$, $F_2XC(X)_n(H)_{2-n}C$, $F_2XCCH_2XCH$, $F_2XCC(X)_n(H)_{2-n}CH_2XCH$, $F_2ClCC(X)_n(H)_{2-n}(CH_3)CH$, $F_2C=CH$, $F_2C=CX$, $F_2XCCH=CH$, $F_2XCXC=CH$, or $F_2XCC(X)_n(H)_{2-n}CH=CH$, in which each X is a halogen atom independently selected from bromo, chloro and fluoro and n is 1 or 2. The most active R groups are $F_2C=CH$, $F_2ClCCH=CH$, $F_2BrC$, and $F_2ClCCH_2BrCH$.

In formula I, m is an integer in the range of 0 to 11. When R has 1 or 3 carbon atoms, m is preferably an even number in the range of 0 to 10. When R has 2 or 4 carbon atoms, m is preferably an odd number in the range of 1 to 11. Thus, in the most active compounds the group $R(CH_2)_m-(R^2)(R^3)C-$ is an even number in the range of 4 to 14 carbon atoms. $R^2$ and $R^3$ are usually hydrogen, but may also be methyl or methylphenylaminocarbonylethyl.

$R^1$ may be hydrogen, lower alkyl, lower alkoxyalkyl, phenyl, lower alkylphenyl, lower alkoxyphenyl, halophenyl, phenylmethyl, lower alkylphenylmethyl, lower alkoxyphenylmethyl, halophenylmethyl, 4H-pyranyl or tri(lower)alkylsilyl, $-C(O)R^4$ or $-P(Z)(YR^5)(OR^6)$.

When $R^1$ is $-C(O)R^4$, $R^4$ may be alkyl, lower cyanoalkyl, lower haloalkyl, triphenylmethyl, phenylmethyl, halophenylmethyl, (phenyl)(halo)methyl, phenoxy(lower)alkyl, (phenoxy)(methoxy)methyl, difluoroethenyl($C_9$)alkyl, difluoroethenyl($C_{10}$)alkoxycarbonyl($C_1$-$C_4$)alkyl, trifluoropyridyloxyphenyl($C_1$-$C_2$)alkyl, alkenyl of 3 to 9 carbon atoms, phenyl(lower)alkenyl, carboxyethenyl, difluorophenylethenyl, ethynyl, $C_1$-$C_2$alkoxy, difluoroethenyl($C_{10}$)alkoxy, difluoroethenyl($C_{10}$)alkoxycarbonyl, phenyl, lower alkylphenyl, halophenyl, $C_1$-$C_2$ alkoxyphenyl, cyanophenyl, nitrophenyl, nitrohalophenyl, fluorophenylcarbonylphenyl, trihaloundecyloxycarbonylphenyl, aminocarbonylphenyl, methylamino, phenylamino, halophenylamino, methylphenylamino, methoxyphenylamino, phenyl($C_1$-$C_2$)alkylamino, or pyrazolyl.

When $R^1$ is $-P(Z)(YR^5)(OR^6)$, Y is monovalent oxygen or sulfur, Z is divalent oxygen or sulfur, one of $R^5$ and $R^6$ is lower alkyl or phenyl, and the other of $R^5$ and $R^6$ is lower alkyl.

In the foregoing description and throughout the specification and claims, unless a contrary intent is clearly expressed, the terms described in this paragraph have the meanings set forth below. Alkyl means a saturated straight or branched hydrocarbyl group of 1-12 carbon atoms. Alkenyl means a straight or branched hydrocarbyl group of 3 to 12 carbon atoms containing one unsaturation. "Lower" as applied to a saturated or unsaturated hydrocarbyl group means 1 to 6, desirably 1 to 4, preferably 1 to 2 carbon atoms. Halogen or halo, alone or modifying other components of a molecule, means one to three hydrogen atoms have been replaced with a corresponding number of halogen atoms selected from bromine, chlorine and fluorine.

The compounds of this invention are illustrated in Table I, below, in which "Ph" designates a phenyl ring, and "Pyr" designates a pyridyl ring.

TABLE I $R-(CH_2)_m-CR^2R^3-OR^1$

| Compound # | R | m | $R^1$ |
|---|---|---|---|
| 1 | $F_2ClC$ | 9 | H |
| 2 | $F_2BrC$ | 4 | H |
| 3 | $F_2BrC$ | 10 | H |
| 4 | $F_3C$ | 9 | H |
| 5 | $F_2ClCClFC$ | 10 | H |
| 6 | $F_5C_2$ | 9 | H |
| 7 | $F_5C_2$ | 10 | H |
| 8 | $F_2ClCCH_2BrCH$ | 2 | H |
| 9 | $F_2ClCCH_2BrCH$ | 7 | H |
| 10 | $F_2ClCCH_2BrCH$ | 8 | H |
| 11 | $F_2BrCCH_2BrCH$ | 2 | H |
| 12 | $F_2BrCCH_2BrCH$ | 3 | H |
| 13 | $F_2BrCCH_2BrCH$ | 7 | H |
| 14 | $F_2BrCCH_2BrCH$ | 8 | H |
| 15 | $F_2ClCCFClCH_2ClCH$ | 0 | H |
| 16 | $F_2ClCCFClCH_2ClCH$ | 1 | H |
| 17 | $F_2ClCCFClCH_2ClCH$ | 2 | H |
| 18 | $F_2ClCCFClCH_2ClCH$ | 7 | H |
| 19 | $F_2ClCCFClCH_2ClCH$ | 8 | H |
| 20 | $F_2ClCCFCl(CH_3)CH$ | 8 | H |
| 21 | $F_2C=CH$ | 1 | H |
| 22 | $F_2C=CH$ | 3 | H |
| 23 | $F_2C=CH$ | 8 | H |
| 24 | $F_2C=CH$ | 9 | H |
| 25 | $F_2C=CH$ | 11 | H |
| 26 | $F_2C=CH$ | 8 | H (1) |
| 27 | $F_2C=CH$ | 8 | H (2) |
| 28 | $F_2C=CH$ | 8 | H (3) |
| 29 | $F_2ClCCH=CH$ | 2 | H |
| 30 | $F_2ClCCH=CH$ | 8 | H |
| 31 | $F_3CCH=CH$ | 7 | H |
| 32 | $F_2ClCFClCCH=CH$ | 8 | H |

TABLE I-continued

R—(CH$_2$)$_m$—CR$^2$R$^3$—OR$^1$

| # | R | m | R$^1$ |
|---|---|---|---|
| 33 | F$_2$ClCCH$_2$BrCH | 7 | —CH$_3$ |
| 34 | F$_2$ClCCH$_2$BrCH | 8 | —CH$_3$ |
| 35 | F$_2$BrCCH$_2$BrCH | 7 | —CH$_3$ |
| 36 | F$_2$BrCCH$_2$BrCH | 8 | —CH$_3$ |
| 37 | F$_2$C=CH | 9 | —CH$_3$ |
| 38 | F$_2$ClCCH=CH | 7 | —CH$_3$ |
| 39 | F$_2$ClCCH=CH | 8 | —CH$_3$ |
| 40 | F$_2$ClCCH=CH | 8 | —C$_3$H$_7$ |
| 41 | F$_2$ClCCH=CH | 8 | —C$_4$H$_9$ |
| 42 | F$_2$BrCCH=CH | 7 | —CH$_3$ |
| 43 | F$_2$BrCCH=CH | 8 | —CH$_3$ |
| 44 | F$_2$ClCCH$_2$BrCH | 3 | —(CH$_2$)$_2$OCH$_3$ |
| 45 | F$_2$ClCFClCCH$_2$ClCH | 3 | —(CH$_2$)$_2$OCH$_3$ |
| 46 | F$_2$ClCCH=CH | 3 | —(CH$_2$)$_2$OCH$_3$ |
| 47 | F$_2$ClCFClCCH=CH | 3 | —(CH$_2$)$_2$OCH$_3$ |
| 48 | F$_2$ClCFClCCH$_2$ClCH | 0 | —Ph |
| 49 | F$_2$C=CH | 9 | —Ph |
| 50 | F$_2$ClCCH=CH | 8 | —Ph |
| 51 | F$_2$C=CH | 9 | 4-CH$_3$Ph— |
| 52 | F$_2$C=CH | 9 | 4-CH$_3$OPh— |
| 53 | F$_2$C=CH | 8 | 4-ClPh— |
| 54 | F$_2$ClCCH=CH | 8 | 4-ClPh— |
| 55 | F$_2$C=CH | 9 | 3,4-Cl$_2$Ph— |
| 56 | F$_2$C=CH | 3 | PhCH$_2$— |
| 57 | F$_2$C=CH | 9 | PhCH$_2$— |
| 58 | F$_2$C=CH | 9 | 4-CH$_3$PhCH$_2$— |
| 59 | F$_2$C=CH | 9 | 4-CH$_3$OPhCH$_2$— |
| 60 | F$_2$C=CH | 9 | 4-ClPhCH$_2$— |
| 61 | F$_2$C=CH | 9 | 3,4-Cl$_2$PhCH$_2$— |

| Compound # | R | m | R$^4$ (A) |
|---|---|---|---|
| 62 | F$_2$BrC | 2 | —CH$_3$ |
| 63 | F$_2$BrC | 4 | —CH$_3$ |
| 64 | F$_2$BrC | 10 | —CH$_3$ |
| 65 | F$_2$BrC | 4 | —CH(CH$_3$)$_2$ |
| 66 | F$_2$BrC | 4 | —CH(C$_3$H$_7$)(C$_2$H$_5$) |
| 67 | F$_2$BrC | 4 | (CH$_3$)$_2$CHC$_4$H$_8$— |
| 68 | F$_2$BrC | 4 | —C$_{10}$H$_{21}$ |
| 69 | F$_2$BrC | 4 | —C$_{11}$H$_{23}$ |
| 70 | F$_2$BrCBrCH | 8 | —CH$_3$ |
| 71 | F$_2$ClCCH$_2$BrCH | 0 | —CH$_3$ |
| 72 | F$_2$ClCCH$_2$BrCH | 8 | —CH$_3$ |
| 73 | F$_2$ClCCH$_2$BrCH | 8 | (CH$_3$)$_3$C— |
| 74 | F$_2$BrCCH$_2$BrCH | 0 | —CH$_3$ |
| 75 | F$_2$BrCCH$_2$BrCH | 2 | —CH$_3$ |
| 76 | F$_2$BrCCH$_2$BrCH | 8 | —CH$_3$ |
| 77 | F$_2$BrCCH$_2$BrCH | 0 | (CH$_3$)$_3$C— |
| 78 | F$_2$BrCCH$_2$BrCH | 8 | (CH$_3$)$_3$C— |
| 79 | F$_2$ClCFClCCH$_2$ClCH | 1 | CH$_3$ |
| 80 | F$_2$ClCFClCCH$_2$ClCH | 8 | CH$_3$ |
| 81 | F$_2$ClCFClCCH$_2$ClCH | 1 | (CH$_3$)$_3$C— |
| 82 | F$_2$C=CH | 8 | CH$_3$ |
| 83 | F$_2$C=CH | 9 | CH$_3$ |
| 84 | F$_2$C=CH | 11 | CH$_3$ |
| 85 | F$_2$C=CH | 9 | —CH(CH$_3$)$_2$ |
| 86 | F$_2$C=CH | 9 | —C(CH$_3$)$_3$ |
| 87 | F$_2$C=CH | 9 | —CH$_2$CH(CH$_3$)$_2$ |
| 88 | F$_2$C=CH | 1 | —CH(C$_2$H$_5$)(C$_4$H$_9$) |
| 89 | F$_2$C=CH | 9 | —CH(C$_2$H$_5$)(C$_4$H$_9$) |
| 90 | F$_2$C=CH | 9 | —CH$_2$C(CH$_3$)$_3$ |
| 91 | F$_2$C=CH | 9 | —C$_2$H$_4$CH(CH$_3$)$_2$ |
| 92 | F$_2$C=CH | 3 | —C$_3$H$_6$CH(CH$_3$)$_2$ |
| 93 | F$_2$C=CH | 9 | —C$_3$H$_6$CH(CH$_3$)$_2$ |
| 94 | F$_2$C=CH | 3 | —C$_4$H$_8$CH(CH$_3$)$_2$ |
| 95 | F$_2$C=CH | 9 | —C$_4$H$_8$CH(CH$_3$)$_2$ |
| 96 | F$_2$C=CH | 9 | —C$_8$H$_{17}$ |
| 97 | F$_2$ClCCH=CH | 8 | —CH$_3$ |
| 98 | F$_2$ClCCH=CH | 8 | —C(CH$_3$)$_3$ |
| 99 | F$_3$CClC=CH | 8 | —CH$_3$ |
| 100 | F$_2$C=CH | 9 | —CH$_2$CN |
| 101 | F$_2$C=CH | 9 | —CCl$_3$ |
| 102 | F$_2$C=CH | 9 | —C(CH$_3$)$_2$CH$_2$Cl |
| 103 | F$_2$ClCCH=CH | 8 | —CF$_3$ |
| 104 | F$_2$C=CH | 9 | —C(Ph)$_3$ |
| 105 | F$_2$C=CH | 9 | —CH$_2$Ph |
| 106 | F$_2$C=CH | 3 | 2-ClPhCH$_2$— |
| 107 | F$_2$C=CH | 3 | 3-ClPhCH$_2$— |
| 108 | F$_2$C=CH | 9 | —CH(Cl)(Ph) |
| 109 | F$_2$C=CH | 9 | —CH$_2$OPh |
| 110 | F$_2$C=CH | 9 | —CH(CH$_3$)OPh |
| 111 | F$_2$C=CH | 9 | —CH(OCH$_3$)OPh |

TABLE I-continued

| | R | $(CH_2)_m$ | $CR^2R^3-OR^1$ |
|---|---|---|---|
| 112 | $F_2C=CH$ | 3 | $-C_9H_{18}CH=CF_2$ |
| 113 | $F_2C=CH$ | 9 | $-CH_2CO_2C_{10}H_{20}CH=CF_2$ |
| 114 | $F_2C=CH$ | 9 | $-C_2H_4CO_2C_{10}H_{20}CH=CF_2$ |
| 115 | $F_2ClCCH=CH$ | 8 | 4-(5-$CF_3$-2-PyrO)PhO($CH_3$)CH— |
| 116 | $F_2BrC$ | 4 | $-CH=CHCH_3$ |
| 117 | $F_2C=CH$ | 3 | $-CH=CHCH_3$ |
| 118 | $F_2C=CH$ | 9 | $-CH=CHCH_3$ |
| 119 | $F_2BrC$ | 4 | $-C(CH_3)=CH_2$ |
| 120 | $F_2C=CH$ | 9 | $-CH_2CH=CH_2$ |
| 121 | $F_2C=CH$ | 3 | $-CH=C(CH_3)_2$ |
| 122 | $F_2C=CH$ | 3 | $-C(CH_3)=CH_2$ |
| 123 | $F_2C=CH$ | 9 | $-C(CH_3)=CH_2$ |
| 124 | $F_2C=CH$ | 3 | $-C(CH_3)=CHCH_3$ |
| 125 | $F_2C=CH$ | 3 | $-CH_2CH(CH_3)C_2H_4CH=C(CH_3)_2$ |
| 126 | $F_2BrC$ | 4 | $-CH=CHPh$ |
| 127 | $F_2C=CH$ | 3 | $-CH=CHPh$ |
| 128 | $F_2BrCCH_2BrCH$ | 8 | $-CH=CHCO_2H$ |
| 129 | $F_2ClCCH=CH$ | 8 | 2,4-$F_2$PhCH=CH— |
| 130 | $F_2ClCCH=CH$ | 8 | 2,6-$F_2$PhCH=CH— |
| 131 | $F_2C=CH$ | 9 | $-C\equiv CH$ |
| 132 | $F_2C=CH$ | 9 | $-OCH_3$ |
| 133 | $F_2C=CH$ | 9 | $-OC_{10}H_{20}CH=CF_2$ |
| 134 | $F_2C=CH$ | 9 | $-CO_2C_{10}H_{20}CH=CF_2$ |
| 135 | $F_2BrC$ | 2 | $-Ph$ |
| 136 | $F_2BrC$ | 10 | $-Ph$ |
| 137 | $F_2BrCBrCH$ | 7 | $-Ph$ |
| 138 | $F_2ClCCH_2BrCH$ | 8 | $-Ph$ |
| 139 | $F_2BrCCH_2BrCH$ | 0 | $-Ph$ |
| 140 | $F_2BrCCH_2BrCH$ | 8 | $-Ph$ |
| 141 | $F_2C=CH$ | 1 | $-Ph$ |
| 142 | $F_2C=CH$ | 2 | $-Ph$ |
| 143 | $F_2C=CH$ | 3 | $-Ph$ |
| 144 | $F_2C=CH$ | 4 | $-Ph$ |
| 145 | $F_2C=CH$ | 5 | $-Ph$ |
| 146 | $F_2C=CH$ | 6 | $-Ph$ |
| 147 | $F_2C=CH$ | 7 | $-Ph$ |
| 148 | $F_2C=CH$ | 8 | $-Ph$ |
| 149 | $F_2C=CH$ | 9 | $-Ph$ |
| 150 | $F_2ClCCH=CH$ | 8 | $-Ph$ |
| 151 | $F_3CClC=CH$ | 1 | $-Ph$ |
| 152 | $F_2C=(Br)C$ | 7 | $-Ph$ |
| 153 | $F_2BrC$ | 10 | 2-$CH_3$Ph |
| 154 | $F_2C=CH$ | 9 | 2-$CH_3$Ph |
| 155 | $F_2C=CH$ | 9 | 3-$CH_3$Ph |
| 156 | $F_2C=CH$ | 9 | 4-$CH_3$Ph |
| 157 | $F_2ClCCH=CH$ | 8 | 2-$CH_3$Ph |
| 158 | $F_2ClCCH=CH$ | 8 | 3-$CH_3$Ph |
| 159 | $F_2ClCCH=CH$ | 8 | 4-$CH_3$Ph |
| 160 | $F_2BrC$ | 10 | 2-ClPh |
| 161 | $F_2BrC$ | 10 | 3-ClPh |
| 162 | $F_2BrC$ | 10 | 4-ClPh |
| 163 | $F_2BrC$ | 10 | 2-FPh |
| 164 | $F_2BrC$ | 10 | 2,3-$Cl_2$Ph |
| 165 | $F_2BrC$ | 10 | 2,4-$Cl_2$Ph |
| 166 | $F_2BrC$ | 10 | 2,5-$Cl_2$Ph |
| 167 | $F_2BrC$ | 10 | 2,6-$Cl_2$Ph |
| 168 | $F_2BrC$ | 10 | 3,4-$Cl_2$Ph |
| 169 | $F_2BrC$ | 10 | 3,5-$Cl_2$Ph |
| 170 | $F_2BrC$ | 10 | 2,4,5-$Cl_3$Ph |
| 171 | $F_2BrC$ | 10 | 3,4,5-$Cl_3$Ph |
| 172 | $F_2BrC$ | 10 | 2,4,6-$Cl_3$Ph |
| 173 | $F_2C=CH$ | 3 | 4-ClPh |
| 174 | $F_2C=CH$ | 9 | 4-ClPh |
| 175 | $F_2C=CH$ | 9 | 3,4-$Cl_2$Ph |
| 176 | $F_2C=CH$ | 9 | 3,5-$F_2$Ph |
| 177 | $F_2C=CH$ | 8 | 3,5-$F_2$Ph (1) |
| 178 | $F_2ClCCH=CH$ | 8 | 2-ClPh |
| 179 | $F_2ClCCH=CH$ | 8 | 4-ClPh |
| 180 | $F_2ClCCH=CH$ | 8 | 2-FPh |
| 181 | $F_2ClCCH=CH$ | 8 | 3-FPh |
| 182 | $F_2ClCCH=CH$ | 8 | 4-FPh |
| 183 | $F_2ClCCH=CH$ | 8 | 2,4-$Cl_2$Ph |
| 184 | $F_2ClCCH=CH$ | 8 | 2,6-$Cl_2$Ph |
| 185 | $F_2ClCCH=CH$ | 8 | 3,4-$Cl_2$Ph |
| 186 | $F_2ClCCH=CH$ | 8 | 3,5-$Cl_2$Ph |
| 187 | $F_2ClCCH=CH$ | 8 | 2,4-$F_2$Ph |
| 188 | $F_2ClCCH=CH$ | 8 | 2,5-$F_2$Ph |
| 189 | $F_2ClCCH=CH$ | 8 | 2,6-$F_2$Ph |
| 190 | $F_2ClCCH=CH$ | 8 | 3,5-$F_2$Ph— |
| 191 | $F_2BrC$ | 10 | 2-$CH_3$OPh— |
| 192 | $F_2C=CH$ | 9 | 4-$CH_3$OPh— |

TABLE I-continued

| | | R—(CH$_2$)$_m$—CR$^2$R$^3$—OR$^1$ | |
|---|---|---|---|
| 193 | F$_2$ClCCH=CH | 8 | 4-CH$_3$OPh— |
| 194 | F$_2$BrC | 10 | 2-CNPh— |
| 195 | F$_2$C=CH | 1 | 4-NO$_2$Ph— |
| 196 | F$_2$ClCCH=CH | 8 | 4-NO$_2$Ph— |
| 197 | F$_2$C=CH | 3 | 2-NO$_2$-4-ClPh— |
| 198 | F$_2$ClCCH=CH | 8 | 2-[4-FPhC(O)]Ph— |
| 199 | F$_2$BrC | 10 | 2-F$_2$BrCC$_{11}$H$_{22}$O$_2$C—Ph |
| 200 | F$_2$BrC | 10 | 2-NH$_2$C(O)Ph |
| 201 | F$_2$ClCCH$_2$BrCH | 8 | —NHCH$_3$ |
| 202 | F$_2$BrCCH$_2$BrCH | 8 | —NHCH$_3$ |
| 203 | F$_2$ClCFClCCH$_2$ClCH | 1 | —NHCH$_3$ |
| 204 | F$_2$ClCCH=CH | 8 | —NHCH$_3$ |
| 205 | F$_2$BrCCH$_2$BrCH | 8 | —NHPh |
| 206 | F$_2$ClCFClCCH$_2$ClCH | 8 | —NHPh |
| 207 | F$_2$C=CH | 9 | —NHPh |
| 208 | F$_2$ClCFClCCH=CH | 8 | —NHPh |
| 209 | F$_2$C=CH | 9 | 4-ClPhNH— |
| 210 | F$_2$C=CH | 9 | 2,4-Cl$_2$PhNH— |
| 211 | F$_2$C=CH | 9 | 4-CH$_3$PhNH— |
| 212 | F$_2$C=CH | 9 | 4-CH$_3$OPhNH— |
| 213 | F$_2$C=CH | 9 | —NH—CH(CH$_3$)—Ph(S-isomer) |
| 214 | F$_2$C=CH | 9 | —NH—CH(CH$_3$)—Ph(chiral) |
| 215 | F$_2$C=CH | 9 | —NCH=CHN=CH |

| Compound # | R | m | Y,Z | R$^5$,R$^6$ (B) |
|---|---|---|---|---|
| 216 | F$_2$C=CH | 9 | 0,0 | C$_2$H$_5$, C$_2$H$_5$ |
| 217 | F$_2$C=CH | 9 | 0,0 | Ph, Ph |
| 218 | F$_2$C=CH | 9 | S,0 | C$_2$H$_5$, CH$_3$ |
| 219 | F$_2$C=CH | 9 | S,0 | C$_2$H$_5$, C$_2$H$_5$ |
| 220 | F$_2$C=CH | 9 | S,0 | C$_3$H$_7$, C$_2$H$_5$ |
| 221 | F$_2$C=CH | 9 | 0,2 | C$_2$H$_5$, C$_2$H$_5$ |

(1) R$^2$ = CH$_3$;
(2) R$^2$ = 4MePhNHC(O)Et
(3) R$^2$, R$^3$ = CH$_3$
(A) R$^1$ = C(O)R$^4$
(B) R$^1$ = P(Z)(yR$^5$)(OR$^6$)

The compounds of the present invention were prepared by methods known to one skilled in the art. Most of the syntheses started with commercially available unsaturated alcohols which were reacted with halofluorocarbons to produce halodifluoroalkanols. The latter were subjected to reactions analogous to known reactions to produce the compounds of the invention.

In one route by which the alcohols were prepared, an omega unsaturated alcohol (I), e.g., 10-undecen-1-ol, was reacted under pressure with a halofluorocarbon, e.g., bromochlorodifluoromethane, in the presence of benzoyl peroxide, yielding 10-bromo-12-chloro-12,12-difluorododecan-1-ol (II). An alternate method utilizes a copper (I) chloride/ethanolamine catalyst in tert.,-butanol rather than benzoyl peroxide. Dehydrobromination of (II) with 1,8-diazabicyclo[5.4.0]undec-7-ene (DBU) yielded 12-chloro-12,12-difluoro-10-dodecen-1-ol (III). Catalytic hydrogenation of (II), however, would afford the corresponding 12-chloro-12,12-difluorododecan-1-ol (IV) by hydrogenolysis of the bromine atom. Examples 1 and 2 illustrate this route of preparation.

Other primary and secondary alcohols of the present invention were also prepared from commercially available omega unsaturated alcohols by a second route. An unsaturated alcohol (I), e.g., 10-undecen-1-ol, was first oxidized to 10-undecen-1-al (V) by the Swern oxidation using oxalyl chloride, dimethyl sulfoxide, and triethylamine in methylene chloride. This aldehyde was then reacted with dibromodifluoromethane, triphenylphosphine, and powdered zinc in dimethylacetamide, producing 1,1-difluoro-1,11-dodecadiene (VI). In order to prepare a secondary alcohol from (VI), the latter was reacted with mercuric acetate in tetrahydrofuran and water and then with sodium borohydride and aqueous sodium hydroxide, producing 12,12-difluoro-11-dodecen-2-ol (VII). Oxidation of (VII) with Jones reagent in acetone yielded methyl 10,10-difluoro-9-decenyl ketone (VIII) which could in turn be reacted with a Grignard reagent, e.g., methylmagnesium bromide, to produce 2-methyl-12,12-difluoro-11-dodecen-2-ol (IX), a tertiary alcohol. Synthesis of primary alcohols was accomplished by reacting (VI) with borane tetrahydrofuran complex and then with sodium hydroxide and hydrogen peroxide, yielding 12,12-difluoro-11-dodecen-1-ol (X). Examples 3, 4, and 5 detail the methods employing this route.

To prepare the ethers of this invention the same commercially available omega unsaturated alcohol (I), e.g. 10-undecen-1-ol, was reacted with an alkyl halide, e.g., iodomethane to produce an ether, methyl 10-undecenyl ether in this illustration. Reaction of this ether with bromochlorodifluoromethane was followed by dehydrobromination using DBU as described above, producing methyl 12-chloro-12,12-difluoro-10-dodecenyl ether (XIII). These reactions are detailed in Example 6.

Additional reaction sequences were also used to prepare ethers of this invention. A two-step method started with the unsaturated alcohol (III), e.g., 12-chloro-12,12-difluoro-10-dodecen-1-ol. Treatment of this alcohol with phosphorus tribromide yielded 12-chloro-12,12-difluoro-10-dodecenyl bromide (XIV) which in turn could be reacted with an alcohol or, preferably, a phenol e.g., 4-chlorophenol, in the presence of DBU in diethyl ether. This sequence of reactions produced 12-chloro-12,12-difluoro-10-dodecenyl 4-chlorophenyl ether (XIII). Alternatively, (III) could be reacted with potassium hydroxide in dimethyl sulfoxide and then with an alkyl halide, e.g., iodobutane, producing butyl 12-chloro-12,12-difluoro-10-dodecenyl ether (XIII). These reactions are detailed in Examples 7 and 8.

Other one-step methods of synthesizing ethers started with alcohol (X). In one method the alcohol, e.g., 12,12-difluoro-11-dodecen-1-ol, was reacted with a phenol, e.g., 4-methylphenol, in the presence of triphenylphosphine and diethyl azodicarboxylate in tetrahydrofuran, producing 12,12-difluoro-11-dodecenyl 4-methylphenyl ether (XV). Alternatively, the same alcohol was reacted with sodium hydride in tetrahydrofuran and then with an alkyl or aralkyl halide, e.g., phenylmethyl bromide, yielding 12,12-difluoro-11-dodecenyl phenylmethyl ether (XV). Examples 9 and 10 detail these synthesis reactions.

Another multi-step synthesis of ethers started with the reaction of a commercially available alkylene diol, e.g., 1,6-pentanediol, with an alkyl or aralkyl halide, e.g., phenylmethyl bromide, in the presence of potassium hydroxide in xylene solvent, yielding 7-phenyl-6-oxaheptan-1-ol (XVI). Oxidation of (XVI) with pyridinium chlorochromate produced the corresponding aldehyde, 7-phenyl-6-oxaheptanal (XVII). Reaction of (XVII) with dibromodifluoromethane, triphenylphosphine, and powdered zinc in dimethylacetamide provided 6,6-difluoro-5-hexenyl phenylmethyl ether (XVIII). This synthesis is detailed in Example 11.

The methods by which esters, carbamate esters, and (thio)phosphate esters were synthesized include the reaction of an alcohol, e.g., 12,12-difluorododecan-1-ol (IV), or a commercially available alcohol, e.g., allyl alcohol, with a carboxylic acid chloride in pyridine or 4-dimethylaminopyridine. Acetate esters were prepared by the reaction of acetic anhydride with an alcohol, e.g., 12,12-difluoro-11-dodecen-1-ol, in the presence of 47% hydrobromic acid or methanesulfonic acid. Compounds having a primary, i.e., displaceable, halogen were esterified with a carboxylic acid, e.g., 4-chlorobenzoic acid, in the presence of DBU. Acid-sensitive compounds, e.g., 3-chloro-1,1-diethoxypropane, were esterified with an alkali metal salt of a carboxylic acid, e.g., sodium benzoate by refluxing the two reactants in dimethylformamide. Phosphate and thiophosphate esters were prepared by the reaction of an alcohol, e.g., 12,12-difluoro-11-dodecen-1-ol, with the phosphoryl chloride in the presence of triethylamine and 4-dimethylaminopyridine.

Carbamate esters were prepared by the reaction of an isocyanate, e.g., phenyl isocyanate, with an alcohol, e.g., 12,12-difluoro-11-dodecen-1-ol, in the presence of dibutyltin diacetate as a catalyst.

After ester formation, additional reactions, most of which are described above, were utilized to further modify the esters themselves. For example, 9,10-dibromo-10,10-difluorodecyl benzoate (XXVI) was prepared by adding elemental bromine to 10,10-difluoro-9 decenyl benzoate (XXV). Subsequently, 9,10-dibromo-10,10-difluorodecyl benzoate was dehydrobrominated using sodium hydride in tetrahydrofuran, yielding 9-bromo-10,10-difluoro-9-decenyl benzoate (XXVII). In order to extend a hydrocarbon chain by three carbon atoms, an unsaturated ester, e.g., 9-decenyl acetate, was reacted with borane-tetrahydrofuran complex and then with acrolein in the presence of hydrochloric acid, producing 13-oxotridecyl acetate (XXIX). As an alternative to catalytic hydrogenolysis to remove a bromine atom, a brominated compound, e.g., 2,4-dibromo-4,4-difluorobutyl acetate (XXXVI), tributyltin hydride, and 1,1'-azobisisobutyronitrile were heated at 120° C., yielding 4-bromo-4,4-difluorobutyl acetate. These reactions are detailed in Examples 12-23.

EXAMPLE 1

SYNTHESIS OF 12-CHLORO-12,12-DIFLUORO-10-DODECEN-1-OL

Compound 30

Step A

Synthesis of a mixture of 10-bromo-12-chloro-12,12-difluorododecan-1-ol (Compound 3-FMC 93935) and 12-chloro-12,12-difluoro-10-dodecen-1-ol Three 200 ml pressure bottles were each charged with 8.5 grams (0.05 mole) of 10-undecen-1-ol, 16.5 grams (0.10 mole) of bromochlorodifluoromethane, 3.0 ml (0.05 mole) of 2-aminoethanol, and 0.05 gram (0.0005 mole) of copper (I) chloride in 50 ml of tert-butanol. The bottles were sealed, and the contents of each were stirred at 70°±5° C. for two days. The reaction mixtures were cooled, and the bottles were opened. Each reaction mixture was stirred with pentane until a dark oil precipitated. The pentane extracts were decanted from the oil precipitates and combined. The combination was concentrated under reduced pressure to a residual oil. This residual oil was distilled under reduced pressure using a Vigreaux distilling column. Two fractions (16.8 grams; b.p. 133° C./0.55 mm) from the distillation were combined with two like fractions (5.7 grams) from a previous run of this reaction, yielding 22.0 grams of 89% pure 10-bromo-12-chloro-12,12-difluorododecan-1-ol. Other fractions from this (14.7 grams) and a previous run of this reaction were combined, yielding 18.1 grams of material that was 49% 10-bromo-12-chloro-12,12-difluorododecan-1-ol and 51% 12-chloro-12,12-difluoro-10-dodecen-1-ol. The mixture was used as an intermediate in the subsequent reaction.

Step B

Synthesis of 12-chloro-12,12-difluoro-10-dodecen-1-ol

A 15.75 gram sample of the mixture of 10-bromo-12-chloro-12,12-difluorododecan-1-ol (6.52 grams; 0.0194 mole) and 12-chloro-12,12-difluoro-10-dodecen-1-ol prepared in Step A of this Example was stirred, and 3.19 ml (0.0213 mole) of 1,8-diazabicyclo[5.4.0]undec-7-ene (DBU) was added slowly. Upon completion of addition, the reaction mixture was stirred until a solid precipitated. Gas chromatographic (GC) analysis of the reaction mixture indicated the presence of approximately 11% of the 10-bromo intermediate. An additional 0.5 ml of DBU was added to the reaction mixture and stirring was continued for an additional 18 hours. The reaction mixture was filtered, and the filtrate was washed with three portions of water. The organic layer was dried with sodium sulfate and then was filtered. The filtrate was concentrated under reduced pressure to a residual oil. The oil was distilled under reduced pressure using a Vigreaux distilling column. The appropriate fractions were combined yielding 9.76 grams of 12-chloro-12,12-difluoro-10-dodecen-1-ol; b.p. 109°-115° C./0.55 mm.

The nmr spectrum was consistent with the proposed structure.

EXAMPLE 2

SYNTHESIS OF 6-BROMO-6,6-DIFLUOROHEXAN-1-OL

Compound 2

Step A

Synthesis of 4,6-dibromo-6,6-difluorohexan-1-ol as an intermediate (Compound 11)

A 200 ml pressure bottle was charged with 17.2 grams (0.2 mole) of 4-penten-1-ol, and the bottle and contents were cooled in an ice bath. To the bottle was added 83.6 grams (0.04 mole) of dibromodifluoromethane and then 1.0 gram of benzoyl peroxide. The bottle was sealed, and it was slowly warmed to 63°±2° C. where the reaction mixture stirred for 18 hours. The bottle was cooled in an ice bath, opened, and 100 ml of pentane was added. The pentane extract was washed with four 25 ml portions of an aqueous solution saturated with sodium bicarbonate. The organic layer was dried with sodium sulfate and filtered. The filtrate was concentrated at 40° C. under reduced pressure to a residual oil. The nmr spectrum indicated only the presence of starting 4-penten-1-ol. The reaction was run again as described above differing in that the reaction mixture was heated at 80° C. for 18 hours. The reaction mixture was worked up as previously described. The starting material was removed from the residual oil by distillation. The residue was evacuated at 105° C./0.2 mm to remove additional volatile material. The yield of 4,6-dibromo-6,6-difluorohexan-1-ol was 11.6 grams as an oil. The nmr spectrum was consistent with the proposed structure.

Step B

Synthesis of 6-bromo-6,6-difluorohexan-1-ol

Under a nitrogen atmosphere, 2.0 grams of 10% palladium on charcoal was weighed into a 500 ml Parr hydrogenation bottle. To the bottle was then added a solution of 11.0 grams (0.037 mole) of 4,6-dibromo-6,6-difluorohexan-1-ol in 75 ml of absolute ethanol. An additional 75 ml of absolute ethanol was used to wash any remaining hexan-1-ol from its container into the hydrogenation bottle. Sodium acetate, 3.1 grams (0.037 mole), was then added to the bottle, and the bottle was placed in the Parr hydrogenator. Upon completion of the uptake of the theoretical amount of hydrogen, the bottle was removed from the hydrogenator, and the contents were filtered. The filtrate was concentrated under reduced pressure to a residual solid. The solid was stirred in 100 ml of pentane, and the mixture was filtered. The filtrate was concentrated under reduced pressure to a residual oil. The oil was purified by column chromatography on silica gel. Elution was accomplished using methylene chloride followed by ethyl acetate. The appropriate fractions were combined and concentrated under reduced pressure yielding 2.0 grams of 6-bromo-6,6-difluorohexan-1-ol. The nmr spectrum was consistent with the proposed structure.

EXAMPLE 3

SYNTHESIS OF 12,12-DIFLUORO-11-DODECEN-2-OL

Compound 26

Step A

Synthesis of 10-undecenal as an intermediate

Under an argon atmosphere, a stirred solution of 82.0 grams (0.646 mole) of oxalyl chloride in 600 ml of methylene chloride was cooled to −50° to −60° C., and a solution of 100.9 grams (1.292 moles) of dimethyl sulfoxide in 120 ml of methylene chloride was added dropwise during a 10-15 minute period. The reaction mixture temperature was maintained at −50° to −60° C. during the addition. Upon completion of addition, the reaction mixture was stirred for two minutes, and then a solution of 100.0 grams (0.587 mole) of 10-undecen-1-ol in 130 ml of methylene chloride was added dropwise during a 15 minute period while maintaining the reaction mixture temperature at −50° to −60° C. Upon completion of addition, the reaction mixture was stirred for 15 minutes, and then 297.1 grams (2.936 moles) of triethylamine was added dropwise during a five minute period while still maintaining the reaction mixture temperature at −50° to −60° C. Upon completion of addition, the reaction mixture was stirred as it was allowed to warm to ambient temperature. After this time 700 ml of water was stirred with the reaction mixture. The water layer was separated and washed with two 160 ml portions of methylene chloride. The washes were combined with the organic layer, and the combination was washed with three 160 ml portions of an aqueous solution saturated with sodium chloride. The organic layer was dried with magnesium sulfate and was then filtered. The filtrate was concentrated under reduced pressure to an oil/solid residue. The residue was stirred with 400 ml of pentane, and the solid was separated by filtration. The filtrate was concentrated under reduced pressure yielding 101.4 grams of 10-undecenal as an oil. The ir spectrum was consistent with the proposed structure.

Step B

Synthesis of 1,1-difluoro-1,11-dodecadiene as an intermediate

Under an argon atmosphere, a stirred mixture of 101.0 grams (0.60 mole) of 10-undecenal and 251.9 grams (1.20 moles) of dibromodifluoromethane was cooled to 0° to −5° C., and a solution of 314.9 grams (1.20 moles) of triphenylphosphine in 1100 ml of N,N-dimethylacetamide was added dropwise during a five to ten minute period. Upon completion of addition, the reaction mixture was allowed to warm to ambient temperature where it was stirred for two hours. After this time a small portion from 70.5 grams (1.20 mole) of zinc powder was added to the reaction mixture. The reaction mixture was warmed to approximately 34° C. with an external heat source to initiate further reaction. Upon commencement of the reaction, the reaction mixture temperature rose to 44° C. The remainder of the 70.5 grams of zinc powder was added portionwise during a ten to twenty minute period. Upon completion of addition, the reaction mixture was warmed to 85°-90° C. where it stirred vigorously for two hours. After this time the reaction mixture was cooled to ambient temperature, and 400 ml of water was added. The reaction mixture was stirred for 30 minutes and then was allowed to stand for 18 hours. After this time the reaction mixture was subjected to a steam distillation using pentane as the extraction solvent. The pentane distillate was concentrated under reduced pressure to a residual oil. The residual oil was heated at 94° C. to remove any N,N-dimethylacetamide. The remaining oil was distilled under reduced pressure, yielding 24.3 grams of 1,1-difluoro-1,11-dodecadiene; b.p. 133° C./66 mm. The nmr spectrum was consistent with the proposed structure.

Step C

Synthesis of 12,12-difluoro-11-dodecen-2-ol

Under an argon atmosphere 6.3 grams (0.02 mole) of mercuric acetate was placed in a reaction vessel. To this was added 20 ml of water and then 20 ml of tetrahydrofuran. The reaction mixture was cooled, and 4.0 grams (0.02 mole) of 1,1-difluoro-1,11-dodecadiene was added dropwise while maintaining the reaction mixture temperature at 25° C. or lower. Upon completion of addition, the reaction mixture was stirred for 20 minutes. After this time 20 ml of an aqueous 3 Molar solution of sodium hydroxide was added dropwise while maintaining the reaction mixture temperature at 25° C. or below. Sodium borohydride, 0.38 gram (0.01 mole), was dissolved in another 20 ml of the aqueous 3 Molar solution of sodium hydroxide, and this was also added dropwise. The reaction mixture temperature was also maintained at 25° C. or below throughout the latter addition. Upon completion of addition, stirring of the reaction mixture was stopped, and mercury was allowed to settle to the bottom of the reaction vessel. Sufficient sodium chloride was added to the reaction mixture to saturate the water layer. The organic layer was then decanted from the reaction mixture and was dried with magnesium sulfate. The mixture was filtered, and the filtrate was concentrated under reduced pressure to a residual oil. The oil was distilled under reduced pressure, yielding 0.53 gram of 12,12-difluoro-11-dodecen-2-ol; b.p. 120° C./3.6 mm. The nmr spectrum was consistent with the proposed structure.

EXAMPLE 4

SYNTHESIS OF 12,12-DIFLUORO-2-METHYL-11-DODECEN-2-OL

Compound 28

Step A

Synthesis of methyl 10,10-difluoro-9-decenyl ketone as an intermediate

To a stirred solution of 1.0 gram (0.0045 mole) of 12,12-difluoro-11-dodecen-2-ol (prepared in Example 3) in 10 ml of acetone was added 1.68 ml (0.0045 mole) of Jones reagent (2.7 Molar in acetone) while maintaining the reaction mixture temperature at 20°–25° C. Excess Jones reagent was destroyed by the addition of 1-methylethanol. The reaction mixture was passed through silica gel with the aid of additional acetone. The eluate was concentrated under reduced pressure, and the residue was dissolved in 50 ml of pentane. The resultant solution was washed with two 20 ml portions of water and then with one 20 ml portion of an aqueous solution saturated with sodium chloride. The organic layer was dried with magnesium sulfate and filtered. The filtrate was concentrated under reduced pressure yielding 0.65 gram of methyl 10,10-difluoro-9-decenyl ketone. The nmr spectrum was consistent with the proposed structure. The reaction was repeated several times.

Step B

Synthesis of 12,12-difluoro-2-methyl-11-dodecen-2-ol

Under a nitrogen atmosphere, a stirred solution of 2.0 grams (0.009 mole) of methyl 10,10-difluoro-9-decenyl ketone in 25 ml of diethyl ether was cooled to 0° C., and 2.96 ml (0.009 mole) of methylmagnesium bromide (3.1 Molar solution) was added via syringe. Upon completion of addition, the reaction mixture was allowed to warm to ambient temperature. Analysis of the reaction mixture by gas chromatography indicated that the reaction had stopped at approximately 50% of completion. An additional 3.0 ml of methylmagnesium bromide was added via syringe, and the reaction mixture was allowed to stir for 18 hours. After this time the reaction mixture was poured into 20 ml of ice containing 5 ml of an aqueous 10% hydrochloride acid solution. The aqueous layer was separated and washed with three 10 ml portions of diethyl ether. The extracts were combined with the organic layer, and the combination was washed with three 10 ml portions of water. The organic layer was dried with magnesium sulfate and filtered. The filtrate was concentrated under reduced pressure to a residual oil. The oil was subjected to column chromatography on silica gel. Elution was accomplished with methylene chloride and then with methanol. The appropriate fractions were combined and concentrated under reduced pressure yielding 1.1 grams of 12,12-difluoro-2-methyl-11-dodecen-2-ol. The nmr spectrum was consistent with the proposed structure.

EXAMPLE 5

SYNTHESIS OF 12,12-DIFLUORO-11-DODECEN-1-OL

Compound 23

Three grams (0.o15 mole) of 1,1-difluoro-1,11-dodecadiene (prepared in Example 3, Step B) was stirred while being cooled to 0° C. After this time 5 ml (0.005 mole) of borane-tetrahydrofuran complex (1 Molar in tetrahydrofuran) was added dropwise. Upon completion of addition, the reaction mixture was stirred for 30 minutes, and then, in turn, 5 ml of aqueous 3 Normal sodium hydroxide and 5 ml of aqueous 30% hydrogen peroxide were added dropwise. Upon completion of addition, the reaction mixture was allowed to warm to ambient temperature where it was stirred for 18 hours. The reaction mixture was concentrated under reduced pressure to a residue. The residue was stirred with 25 ml of water, and the mixture was extracted with three 15 ml portions of methylene chloride. The combined extracts were washed with two 15 ml portions of an aqueous solution saturated with sodium chloride. The organic layer was dried with magnesium sulfate and filtered. The filtrate was concentrated under reduced pressure to a residual oil. The oil was evacuated under reduced pressure at 135° C., and then it was subjected to column chromatography on silica gel. Elution was accomplished using heptane and methylene chloride. The appropriate fractions were combined and concentrated under reduced pressure yielding 0.74 gram of 12,12-difluoro-11-dodecen-1-ol. The nmr spectrum was consistent with the proposed structure.

EXAMPLE 6

SYNTHESIS OF 12-CHLORO-12,12-DIFLUORO-10-DODECENYL METHYL ETHER

Compound 39

Step A

Synthesis of methyl 10-undecenyl ether as an intermediate

Under an argon atmosphere a stirred mixture of 15.5 grams (0.375 mole) of sodium hydride (60% in mineral oil) in 180 ml of tetrahydrofuran was warmed to 50° C., and 28 ml (0.45 mole) of iodomethane was added portionwise. Upon completion of addition, 41.1 grams (0.24 mole) of 10-undecen-1-ol in 75 ml of tetrahydrofuran was added dropwise during a one hour period. Upon completion of addition, the reaction mixture was heated at 50° C. for an additional 90 minutes, and then it was allowed to cool to ambient temperature where it stirred for 60 hours. The reaction mixture was cooled in an ice water bath, and cold water was added dropwise until all of the solid material in the reaction mixture was dissolved. The aqueous layer was extracted with two portions of diethyl ether, and the ether extracts were combined with the organic layer from the reaction mixture. The organic layer extract combination was washed in turn with 50 ml of water and 50 ml of an aqueous solution saturated with sodium chloride. The organic layer was dried with sodium sulfate and filtered. The filtrate was concentrated at atmospheric pressure to a residue. The residue was distilled under reduced pressure, yielding 36.1 grams of methyl 10-undecenyl ether; b.p. 99°-100° C./5.5 mm.

Step B

Synthesis of 10-bromo-12-chloro-12,12-difluorododecanyl methyl ether (Compound 34) as an intermediate This compound was prepared in a manner analogous to that of Example 1, Step A, using 5.5 grams (0.03 mole) of methyl 10-undecenyl ether, 12 grams (excess) of bromochlorodifluoromethane, 1.8 ml (0.03 mole) of 2-aminoethanol, and 0.03 gram (0.0003 mole) of copper (I) chloride in 35 ml of tetrahydrofuran. The yield of 10-bromo-12-chloro-12,12-difluorododecanyl methyl ether was 3.5 grams. The nmr spectrum was consistent with the proposed structure.

Step C

Synthesis of 12-chloro-12,12-difluoro-10-dodecenyl methyl ether

This compound was prepared in a manner analogous to that of Example 1, Step B, using 2.8 grams (0.008 mole) of 10-bromo-12-chloro-12,12-difluorododecanyl methyl ether and 1.8 ml (0.012 mole) of DBU. The yield of 12-chloro-12,12-difluoro-10-dodecenyl methyl ether was 1.0 gram. The nmr spectrum was consistent with the proposed structure.

EXAMPLE 7

SYNTHESIS OF 12-CHLORO-12,12-DIFLUORO-10-DODECENYL 4-CHLOROPHENYL ETHER

Compound 54

Step A

Synthesis of 12-chloro-12,12-difluoro-10-dodecenyl bromide as an intermediate

Under an argon atmosphere 4.8 grams (0.019 mole) of 12-chloro-12,12-difluoro-10-dodecen-1-ol (prepared in Example 1) was stirred, and 0.65 ml (0.007 mole) of phosphorus tribromide was added dropwise using a syringe. Upon completion of addition, the reaction mixture was stirred at ambient temperature for 18 hours. After this time the reaction mixture was poured into 100 ml of ice/water with stirring. An additional 300 ml of water was added to the gelatinous mixture, and stirring was continued for 18 hours. The mixture was extracted with pentane, and the extract was washed with aqueous sodium bicarbonate. Additional water was added to help separate the layers. The organic layer was washed with an aqueous solution saturated with sodium chloride and then was dried with sodium sulfate. The mixture was filtered, and the filtrate was concentrated under reduced pressure yielding 4.4 grams of 12-chloro-12,12-difluoro-10-dodecenyl bromide. The nmr spectrum was consistent with the proposed structure.

Step B

Synthesis of 12-chloro-12,12-difluoro-10-dodecenyl 4-chlorophenyl ether

A mixture of 1.6 grams (0.005 mole) of 12-chloro-12,12-difluoro-10-dodecenyl bromide and 0.65 gram (0.005 mole) of 4-chlorophenol was stirred, and 0.75 ml (0.005 mole) of DBU was added dropwise. Upon completion of addition, the reaction mixture was stirred at ambient temperature for 18 hours. Gas chromatographic analysis of the reaction mixture indicated the presence of the bromide starting material. An additional 0.5 ml of DBU was added, and the reaction mixture was stirred for 18 hours more. After this time the reaction mixture was shaken with heptane and water. The heptane layer was washed with several portions of water and then with two portions of an aqueous solution saturated with sodium chloride. The organic layer was dried with sodium sulfate and filtered. The filtrate was concentrated under reduced pressure to a residual oil. The oil was subjected to column chromatography on silica gel. Elution was accomplished using in succession heptane, 20% ethyl acetate in heptane, and 5% ethanol in heptane. The appropriate fractions were combined and concentrated under reduced pressure yielding 0.56 gram of 12-chloro-12,12-difluoro-10-dodecenyl 4-chlorophenyl ether. The nmr spectrum was consistent with the proposed structure.

EXAMPLE 8

SYNTHESIS OF BUTYL 12-CHLORO-12,12-DIFLUORO-10-DODECENYL ETHER

Compound 41

A mixture of 3.3 grams (0.0129 mole) of 12,12-difluoro-10-dodecen-1-ol (prepared in Example 1), 1.3 grams (0.0224 mole) of potassium hydroxide and 5 ml of dimethylsulfoxide was stirred for two hours, and then 1.72 ml (0.0151 mole) of iodobutane was added dropwise. Upon completion of addition, the reaction mixture was stirred at ambient temperature for 60 hours. After this time the reaction mixture was warmed to 70° C. where it was stirred for three hours. The reaction mixture was cooled to ambient temperature and then was poured into ice/water. The mixture was extracted with four portions of heptane. The combined heptane extracts were washed with two portions of water and with one portion of an aqueous solution saturated with sodium chloride. The organic layer was dried with sodium sulfate and filtered. The filtrate was concentrated under reduced pressure to a residual oil. The oil was subjected to column chromatography on silica gel. Elution was accomplished using in succession heptane, 1% ethyl acetate in heptane, and 2% ethanol in heptane. The appropriate fractions were combined and concentrated under reduced pressure yielding 0.65 gram of butyl 12-chloro-12,12-difluoro-10-dodecenyl ether. The nmr spectrum was consistent wit the proposed structure.

EXAMPLE 9

SYNTHESIS OF 12,12-DIFLUORO-11-DODECENYL 4-METHYLPHENYL ETHER

Compound 51

A solution of 1.0 gram (0.0045 mole) of 12,12-difluoro-11-dodecen-1-ol (prepared in Example 5), 0.49 gram (0.0045 mole) of 4-methylphenol, 1.2 grams (0.0045 mole) of triphenylphosphine, and 0.79 gram (0.0045 mole) of diethyl azodicarboxylate in 25 ml of tetrahydrofuran was stirred, and the progress of the reaction was monitored by gas chromatographic analysis. Upon completion of the reaction, the reaction mixture was concentrated under reduced pressure to a residue. The residue was dissolved in 25 ml of diethyl ether, and a solid precipitate was removed by filtration. The filtrate was concentrated under reduced pressure to a residual solid. The solid was subjected to column chromatography on silica gel. Elution was accomplished using methylene chloride. The appropriate fractions were combined and concentrated under reduced pressure yielding 0.52 gram of 12,12-difluoro-11-dodecenyl 4-methylphenyl ether. The nmr spectrum was consistent with the proposed structure.

EXAMPLE 10

SYNTHESIS OF 12,12-DIFLUORO-11-DODECENYL PHENYLMETHYL ETHER

Compound 57

Under a nitrogen atmosphere a stirred mixture of 0.18 gram (0.0075 mole) of sodium hydride in 25 ml of tetrahydrofuran was cooled in an ice-bath, and 1.5 grams (0.0068 mole) of 12,12-difluoro-11-dodecen-1-ol (prepared in Example 5) was added dropwise. Upon completion of addition and when the evolution of hydrogen ceased, a solution of 1.2 grams (0.0068 mole) of phenylmethyl bromide in 5 ml of tetrahydrofuran was added dropwise. Upon completion of addition, the reaction mixture was stirred at ambient temperature for 18 hours. After this time the reaction mixture was taken up in 150 ml of diethyl ether and was washed with 50 ml of water and then with 50 ml of an aqueous solution saturated with sodium chloride. The organic layer was dried with magnesium sulfate and filtered. The filtrate was concentrated under reduced pressure to a residual oil. The oil was subjected to column chromatography on silica gel. Elution was accomplished using methylene chloride. The appropriate fractions were combined and concentrated under reduced pressure yielding 0.8 gram of 12,12-difluoro-11-dodecenyl phenylmethyl ether. The nmr spectrum was consistent with the proposed structure.

EXAMPLE 11

SYNTHESIS OF 6,6-DIFLUORO-5-HEXENYL PHENYLMETHYL ETHER

Compound 56

Step A

Synthesis of 7-phenyl-6-oxaheptan-1-ol as an intermediate

A stirred solution of 107.0 grams (1.0 mole) of 1,5-pentanediol, 30 ml (0.25 mole) of phenylmethyl bromide and 33.0 grams of 85% potassium hydroxide in 40 ml of xylenes was heated at 110° C. for 18 hours. After this time the reaction mixture was cooled and shaken with diethyl ether and water. The organic layer was washed in turn with water, aqueous 5% hydrochloric acid, water, and with an aqueous solution saturated with sodium chloride. The organic layer was dried with magnesium sulfate and filtered. The filtrate was concentrated under reduced pressure to a residual oil. The oil was subjected to column chromatography on silica gel. Elution was accomplished using 0.5–50% diethyl ether in hexanes. The appropriate fractions were combined and concentrated under reduced pressure yielding 27.6 grams of 7-phenyl-6-oxaheptan-1-ol. The nmr spectrum was consistent with the proposed structure.

Step B

Synthesis of 7-phenyl-6-oxaheptan-1-al as an intermediate

Under a nitrogen atmosphere a mixture of 8.0 grams (0.041 mole) of 7-phenyl-6-oxaheptan-1-ol and 1.4 grams of 95% silicon dioxide in 125 ml of methylene chloride was stirred, and 19.8 grams (0.090 mole) of pyridinium chlorochromate was added. Upon completion of addition, the reaction mixture was stirred at ambient temperature for four hours. After this time the reaction mixture was diluted with diethyl ether and then was passed through a column of magnesium silicate. The eluate was concentrated under reduced pressure yielding 6.2 grams of 7-phenyl-6-oxaheptan-1-al. The reaction was repeated.

Step C

Synthesis of 6,6-difluoro-5-hexenyl phenylmethyl ether

This compound was prepared in a manner analogous to that of Example 3, Step B, using 16.0 grams (0.083 mole) of 7-phenyl-6-oxaheptan-1-al, 18 ml (0.190 mole) of dibromodifluoromethane, 103.0 grams (0.393 mole) of triphenylphosphine, and 26.0 grams (0.398 mole) of powdered zinc in 250 ml of dimethylacetamide. The yield of 6,6-difluoro-5-hexenyl phenylmethyl ether was 12.6 grams. The nmr spectrum was consistent with the proposed structure.

EXAMPLE 12

SYNTHESIS OF 6-BROMO-6,6-DIFLUOROHEXYL CINNAMATE

Compound 126

To a stirred solution of 0.95 gram (0.0044 mole) of 6-bromo-6,6-difluorohexan-1-ol (prepared in Example 2) and 1.0 ml of triethylamine in 10 ml of diethyl ether was added 0.80 gram (0.0048 mole) of cinnamoyl chloride. One crystal of dimethylaminopyridine was then added, and the reaction mixture was stirred at ambient temperature for 18 hours. The reaction mixture was diluted with 50 ml of diethyl ether and was washed in turn with 20 ml of water, 20 ml of an aqueous 1N hydrochloric acid solution, 20 ml of water, 20 ml of an aqueous solution saturated with sodium bicarbonate, 20 ml of water, and 20 ml of an aqueous solution saturated with sodium chloride. The organic layer was dried with magnesium sulfate and filtered. The filtrate was concentrated under reduced pressure to a residual oil. The oil was subjected to column chromatography on silica gel. Elution was accomplished using methylene chloride. The yield of 6-bromo-6,6-difluorohexyl cinnamate was 0.90 gram. The nmr spectrum was consistent with the proposed structure.

EXAMPLE 13

SYNTHESIS OF 12,12-DIFLUORO-11-DODECENYL N-PHENYLCARBAMATE

Compound 207

To a stirred solution of 2.0 grams (0.0091 mole) of 12,12-difluoro-11-dodecen-1-ol (prepared in Example 5) in 15 ml of heptane was added two drops of dibutyltin diacetate, and then 1.2 grams (0.0100 mole) of phenyl isocyanate was added dropwise. Upon completion of addition, the reaction mixture was warmed to 80° C. where it stirred for 30 minutes. The reaction mixture was allowed to cool to ambient temperature where it stirred for 18 hours. After this time the reaction mixture was cooled in a freezer, and a precipitate was collected by filtration. The filter cake was washed with cold pentane and dried yielding 2.47 grams of 12,12-difluoro-11-dodecenyl N-phenylcarbamate; m.p. 54°–56° C. The nmr spectrum was consistent with the proposed structure.

EXAMPLE 14

SYNTHESIS OF 12-BROMO-12,12-DIFLUORODODECANYL ACETATE

Compound 64

Acetic anhydride, 37 ml, was added slowly dropwise to 10 ml of stirred 47% hydrobromic acid. Upon completion of addition, 10.0 grams (0.045 mole) of 12,12-difluoro-11-dodecen-1-ol (prepared in Example 5) was added dropwise. Following this addition the reaction mixture was warmed to 100° C. where it was stirred for three hours. The reaction mixture was cooled to ambient temperature and then was extracted with three 20 ml portions of methylene chloride. The combined extracts were in turn washed with one 15 ml portion of water, three 15 ml portions of an aqueous solution saturated with sodium bicarbonate, one 15 ml portion of water, one 15 ml portion of aqueous 1N hydrochloric acid, one 15 ml portion of water and one 15 ml portion of an aqueous solution saturated with sodium chloride. The organic layer was dried with magnesium sulfate and filtered. The filtrate was concentrated under reduced pressure to a residual oil. The oil was subjected to column chromatography on silica gel. Elution was accomplished using 10% ethyl acetate in heptane. The appropriate fractions were combined and concentrated under reduced pressure yielding 2.8 grams of 12-bromo-12,12-difluorododecanyl acetate. The nmr spectrum was consistent with the proposed structure.

EXAMPLE 15

SYNTHESIS OF 2,4-DIBROMO-4,4-DIFLUOROBUTYL TRIMETHYLACETATE

Compound 77

Step A

Synthesis of 2-propenyl trimethylacetate as an intermediate

A stirred solution of 11.6 grams (0.20 mole) of 2-propen-1ol in 100 ml of pyridine was heated to reflux. To this was added dropwise 24.1 grams (0.02 mole) of trimethylacetyl chloride. The exothermic reaction caused the reaction mixture temperature to become excessive. The heat source was removed, and the reaction mixture was cooled in an ice bath. The addition of the acid chloride was continued to completion. Upon completion of addition, the reaction mixture was warmed to reflux where it stirred for one hour. After this time the reaction mixture was cooled to ambient temperature where it stood for 60 hours. The reaction mixture was shaken with 700 ml of water, and the organic layer was separated. The aqueous layer was washed with two 15o ml portions of diethyl ether. The washes and the organic layer were combined and washed with two 75 ml portions of an aqueous solution saturated with sodium chloride. The organic layer was dried with magnesium sulfate and filtered. The filtrate was concentrated under reduced pressure to a residual oil. Low boiling volatile materials were removed from the oil by distillation under reduced pressure (b.p. 87°–100° C./21 mm), yielding 12.3 grams of 2-propenyl trimethylacetate as a residue. The nmr spectrum was consistent with the proposed structure.

Step B

Synthesis of 2,4-dibromo-4,4-difluorobutyl trimethylacetate

This compound was prepared in a manner analogous to that of Example 2, Step A, using 11.4 grams (0.08 mole) of 2-propenyl trimethylacetate, 33.6 grams (0.16 mole) of dibromodifluoromethane, and 1.25 grams of benzoyl peroxide. The yield of 2,4-dibromo-4,4-difluorobutyl trimethylacetate was 4.5 grams; b.p. 120° C./8 mm.

EXAMPLE 16

SYNTHESIS OF 9-BROMO-10,10-DIFLUORO-9-DECENYL BENZOATE

Compound 152

Step A

Synthesis of 9-hydroxynonyl benzoate as an intermediate

To a stirred solution of 51.2 grams (0.320 mole) of 1,9-nonanediol in 500 ml of tetrahydrofuran was added one crystal of p-dimethylaminopyridine, and then 8.9 grams (0.088 mole) of triethylamine was added. To this mixture was added dropwise a solution of 11.2 grams (0.08 mole) of benzoyl chloride in 40 ml of methylene chloride. Upon completion of addition, the reaction mixture was stirred at ambient temperature for 18 hours. The reaction mixture was concentrated under reduced pressure to a residue. The residue was dissolved in 200 ml of methylene chloride and was washed with five 75 ml portions of water. The organic layer was dried with magnesium sulfate and filtered. The filtrate was concentrated under reduced pressure to a residue. Volatile materials were removed by distillation leaving 11.5 grams of 9-hydroxynonyl benzoate. The nmr spectrum was consistent with the proposed structure.

Step B

Synthesis of 9-oxononyl benzoate as an intermediate

This compound was prepared in a manner analogous to that of Example 11, Step B, using 1.0 gram (0.0038 mole) of 9-hydroxynonyl benzoate and 7.4 grams (excess) of pyridinium chlorochromate in 10 ml of methylene chloride. The yield of 9-oxononyl benzoate was 0.4 gram. The nmr spectrum was consistent with proposed structure. The reaction was repeated.

Step C

Synthesis of 10,10-difluoro-9-decenyl benzoate as an intermediate

Compound 147

This compound was prepared in a manner analogous to that of Example 3, Step B, using 12.5 grams (0.046 mole) of 9-oxononyl benzoate, 19.2 grams (0.091 mole) of dibromodifluoromethane, 24.0 grams (0.091 mole) of triphenylphosphine, and 6.0 grams (0.091 mole) of zinc powder in 85 ml of dimethylacetamide. The yield of 10,10-difluoro-9-decenyl benzoate was 3.3 grams. The nmr spectrum was consistent with the proposed structure.

Step D

Synthesis of 9,10-dibromo-10,10-difluorodecyl benzoate as an intermediate

Compound 137

To a stirred solution of 2.7 grams (0.009 mole) of 10,10-difluoro-9-decenyl benzoate in 15 ml of carbon tetrachloride was added dropwise a solution of 1.6 grams (0.01 mole) of bromine in 10 ml of carbon tetrachloride. Upon completion of addition, the reaction mixture was stirred at 40°-45° C. for 30 minutes, and then it was cooled to ambient temperature. The reaction mixture was taken up in 50 ml of methylene chloride and was washed with one 25 ml portion of an aqueous solution saturated with sodium bisulfite and with one 25 ml portion of an aqueous solution saturated with sodium chloride. The organic layer was dried with magnesium sulfate and filtered. The filtrate was concentrated under reduced pressure to a residual oil. The oil was subjected to column chromatography on silica gel. Elution was accomplished using 10% ethyl acetate in heptane. The appropriate fractions were combined and concentrated under reduced pressure yielding 2.0 grams of 9,10-dibromo-10,10-difluorodecyl benzoate. The nmr spectrum was consistent with the proposed structure.

Step E

Synthesis of 9-bromo-10,10-difluoro-9-decenyl benzoate

Under a nitrogen atmosphere a stirred mixture of 0.09 gram (0.0036 mole) of sodium hydride in 10 ml of tetrahydrofuran was cooled in an ice bath, and 0.5 gram (0.0036 mole) of 4-methoxyphenylmethanol was added dropwise. When the evolution of hydrogen ceased, a solution of 1.5 grams (0.0033 mole) of 9,10-dibromo-10,10-difluorodecyl benzoate in 5 ml of tetrahydrofuran was added dropwise. Upon completion of addition, the reaction mixture was allowed to warm to ambient temperature where it stirred for 18 hours. After this time the reaction mixture was taken up in 150 ml of diethyl ether and was washed with 50 ml of water and then with 50 ml of an aqueous solution saturated with sodium chloride. The organic layer was dried with magnesium sulfate and filtered. The filtrate was concentrated under reduced pressure to a residual oil. The oil was subjected to column chromatography on silica gel. Elution was accomplished using methylene chloride. The appropriate fractions were combined and concentrated under reduced pressure yielding 0.44 gram of 9-bromo-10,10-difluoro-9-decenyl benzoate. The nmr spectrum was consistent with the proposed structure.

EXAMPLE 17

SYNTHESIS OF 14,14-DIFLUORO-13-TETRADECENYL ACETATE

Compound 84

Step A

Synthesis of 9-decenyl acetate as an intermediate

Acetic anhydride, 54.0 grams (0.52 mole), was stirred, and one drop (catalyst) of methanesulfonic acid was added. To this was cautiously added dropwise 50.0 grams (0.32 mole) of 9-decen-1-ol. The addition caused an exothermic reaction which warmed the reaction mixture to 30°. C. Upon completion of addition, the reaction mixture was warmed to 60° C. where it stirred for 18 hours. The reaction mixture was cooled and poured into 600 ml of ice/water. The mixture was stirred until the ice melted, and then the layers were separated. The aqueous layer was washed with one 300 ml portion of diethyl ether. The wash was combined with the organic layer, and the combination was washed repeatedly with aqueous 1N sodium hydroxide until the organic layer was basic. The organic layer was dried with sodium sulfate and filtered. The filtrate was concentrated under reduced pressure to a residual oil. The oil was distilled under reduced pressure, yielding 57 grams of 9-decenyl acetate; b.p. 93°-95° C./1.5 mm. The nmr spectrum was consistent with the proposed structure.

Step B

Synthesis of 13-oxotridecyl acetate as an intermediate

To a stirred 1.0 Molar solution of borane-tetrahydrofuran complex, 90 ml (0.09 mole), was added dropwise 57 grams (0.27 mole) of 9-decenyl acetate. The reaction mixture temperature was maintained at 20°–25° C. during the addition. Upon completion of addition, the reaction mixture stirred at ambient temperature for 18 hours. After this time 2 ml of aqueous 3M hydrochloric acid was added, and the reaction mixture was stirred for five minutes. To this was then added 5.0 grams (0.09 mole) of acrolein, during which time the reaction mixture temperature rose to 35° C. The reaction mixture was concentrated under reduced pressure to a residual oil. The oil was taken up in pentane and was washed with three 30 ml portions of an aqueous solution saturated with sodium bicarbonate. The organic layer was concentrated under reduced pressure to a residual oil. Volatile materials were removed from the oil by distillation under reduced pressure yielding 4.9 grams of 13-oxotridecyl acetate. The nmr spectrum was consistent with the proposed structure.

Step C

Synthesis of 14,14-difluoro-13-tetradecenyl acetate

This compound was prepared in a manner analogous to that of Example 3, Step B, using 4.9 grams (0.015 mole) of 13-oxotridecyl acetate, 6.3 grams (0.03 mole) of dibromodifluoromethane, 7.8 grams (0.03 mole) of triphenylphosphine, and 2.0 grams (0.03 mole) of zinc powder in 50 ml of dimethylacetamide. The yield of 14,14-difluoro-13-tetradecenyl acetate was 2.5 grams. The nmr spectrum was consistent with the proposed structure.

EXAMPLE 18

SYNTHESIS OF 4,4-DIFLUORO-3-BUTENYL BENZOATE

Compound 141

Step A

Synthesis of 3-ethoxy-4-oxahexyl benzoate as an intermediate

To a stirred solution of 5.0 grams (0.034 mole) of sodium benzoate in 100 ml of dimethylformamide was added 5.2 grams (0.031 mole) of 3-chloro-1,1-diethoxypropane. Upon completion of addition, the reaction mixture was warmed to reflux where it stirred for four hours. After this time the reaction mixture was cooled to ambient temperature and was filtered to remove a solid. The filtrate was diluted with water, and the mixture was extracted with diethyl ether. The combined extracts were dried with magnesium sulfate and filtered. The filtrate was concentrated under reduced pressure to a residual oil. The nmr spectrum indicated the presence of solvents. The oil was redissolved in diethyl ether and washed with water. The organic layer was dried with magnesium sulfate and filtered. The filtrate was concentrated under reduced pressure to a residual oil. The oil was evacuated under high vacuum yielding 6.3 grams of 3-ethoxy-4-oxahexyl benzoate. The nmr spectrum was consistent with the proposed structure.

Step B

Synthesis of 3-oxopropyl benzoate as an intermediate

To a stirred solution of 5.0 grams (0.020 mole) of 3-ethoxy-4-oxahexyl benzoate in 100 ml of tetrahydrofuran was added 100 ml of aqueous 5% hydrochloric acid. The reaction mixture was stirred at ambient temperature for three hours, and then it was poured into 100 ml of water. The mixture was extracted with two 100 ml portions of diethyl ether. The combined extracts were dried with magnesium sulfate and filtered. The filtrate was concentrated under reduced pressure yielding 1.9 grams of 3-oxopropyl benzoate. The nmr spectrum was consistent with the proposed structure.

Step C

Synthesis of 4,4-difluoro-3-butenyl benzoate

This compound was prepared in a manner analogous to that of Example 3, Step B, using 1.5 grams (0.008 mole) of 3-oxopropyl benzoate, 3.5 grams (0.017 mole) of dibromodifluoromethane, 4.4 grams (0.017 mole) of triphenylphosphine, and 1.1 grams (0.017 mole) of zinc powder in 60 ml of dimethylacetamide. The yield of 4,4-difluoro-3-butenyl benzoate was 0.72 gram. The nmr spectrum was consistent with the proposed structure.

EXAMPLE 19

SYNTHESIS OF 6,6-DIFLUORO-5-HEXENYL 4-CHLOROBENZOATE

Compound 173

Step A

Synthesis of 5-chloropentanal as an intermediate

This compound was prepared in a manner analogous to that of Example 11, Step B, using 50.0 grams (0.408 mole) of 5-chloropentan-1-ol and 193.0 grams (0.895 mole) of pyridinium chlorochromate in 400 ml of methylene chloride. The yield of 5-chloropentanal was 34.1 grams. The nmr spectrum was consistent with the proposed structure.

Step B

Synthesis of 6-chloro-1,1-difluoro-1-hexene as an intermediate

This compound was prepared in a manner analogous to that of Example 3, Step B, using 34.0 grams (0.191 mole) of 5-chloropentanal, 118.2 grams (0.382 mole) of dibromodifluoromethane, 150.0 grams (o.3B2 mole) of triphenylphosphine, and 36.8 grams (0.382 mole) of powdered zinc in 130 ml of dimethylacetamide. The yield of 6-chloro-1,1-difluoro-1-hexene was 9.5 grams. The nmr spectrum was consistent with the proposed structure.

Step C

Synthesis of 6,6-difluoro-5-hexenyl 4-chlorobenzoate

Compound 201

Under a nitrogen atmosphere a solution of 2.7 grams (0.0171 mole) of 4-chlorobenzoic acid in 100 ml of acetonitrile was stirred, and 2.6 grams (0.0171 mole) of DBU was added. Upon completion of addition, the reaction mixture was stirred at ambient temperature for 15 minutes, and then 4.0 grams (0.017 mole) of 6-chloro-1,1-difluoro-1-hexene was added. The reaction mixture was then warmed to and stirred at reflux for 18 hours. The reaction mixture was cooled and was washed into a separatory funnel with diethyl ether. The reaction mixture was washed in turn with 50 ml of aqueous 10% hydrochloric acid, 50 ml of aqueous 10% sodium bicarbonate, and 50 ml of an aqueous solution saturated with sodium chloride. The organic layer was dried with magnesium sulfate nd filtered. The filtrate was concentrated under reduced pressure to a residual oil. The oil was subjected to column chromatography on silica gel. Elution was accomplished using 5% diethyl ether in hexane. The appropriate fractions were combined and concentrated under reduced pressure yielding 3.9 grams of 6,6-difluoro-5-hexenyl 4-chlorobenzoate. The nmr spectrum was consistent with the proposed structure.

EXAMPLE 20

SYNTHESIS OF 4-BROMO-4,4-DIFLUOROBUTYL ACETATE

Compound 62

Step A

Synthesis of 2,4-dibromo-4,4-difluorobutyl acetate as an intermediate

Compound 74

This compound was prepared in a manner analogous to that of Example 2, Step A, using 10 ml (0.1 mole) of 2-propenyl acetate, 17.5 ml (0.2 mole) of dibromodifluoromethane, and 1.2 grams (catalyst) of benzoyl peroxide. The yield of 2,4-dibromo-4,4-difluorobutyl acetate was 9.1 grams; b.p. 47°–48° C./;0.1–0.15 mm. The nmr spectrum was consistent with the proposed structure.

Step B

Synthesis of 4-bromo-4,4-difluorobutyl acetate

A solution of 8.6 grams (0.028 mole) of 2,4-dibromo-4,4-difluorobutyl acetate and 8.2 ml (0.028 mole) of tributyltin hydride in 15 ml of xylene was stirred, and 0.01 gram of 1,1'-azobisisobutyronitrile was added. The reaction mixture was warmed to 120° C. where it was stirred for 18 hours. The reaction mixture was distilled under reduced pressure, yielding 0.4 gram of 4-bromo-4,4-difluorobutyl acetate; b.p. 40°–55° C./1.8 mm. The nmr spectrum was consistent with the proposed structure.

EXAMPLE 21

SYNTHESIS OF 4-BROMO-4,4-DIFLUOROBUTYL BENZOATE

Compound 135

Step A

Synthesis of 2,4-dibromo-4,4-difluorobutyl benzoate as an intermediate

This compound was prepared in a manner analogous to that of Example 2, Step A, using 30.0 grams (0.185 mole) of 2-propenyl benzoate, 69.9 grams (0.333 mole) of dibromodifluoromethane and 4.5 grams (0.019 mole) of benzoyl peroxide. The yield of 2,4-dibromo-4,4-difluorobutyl benzoate was 18.5 grams. The nmr spectrum was consistent with the proposed structure.

Step B

Synthesis of 4-bromo-4,4-difluorobutyl benzoate

This compound was prepared in a manner analogous to that of Example 2, Step B, using 15.8 grams (0.042 mole) of 2,4-dibromo-4,4-difluorobutyl benzoate, 3.5 grams (0.042 mole) of sodium acetate, 2.0 grams (catalyst) of palladium on carbon, and hydrogen in 100 ml of ethanol. The yield of 4-bromo-4,4-difluorobutyl benzoate was 8.4 grams. The nmr spectrum was consistent with the proposed structure.

EXAMPLE 22

SYNTHESIS OF O-ETHYL S-PROPYL O-(12,12-DIFLUORO-11-DODECENYL) THIOPHOSPHATE

Compound 220

Step A

Synthesis of S-propyl thiophosphoryl dichloride as an intermediate

A stirred solution of 15.0 grams (0.197 mole) 1-propanethiol in 150 ml of toluene was cooled in an ice/water bath, and 29.3 grams (0.217 mole) of sulfuryl chloride was added dropwise during a 40 minute period. After this time 11.8 grams (0.197 mole) of acetic acid was added, and then 27.2 grams (0.197 mole) of phosphorus trichloride was slowly added. Upon completion of addition, the reaction mixture was allowed to warm to ambient temperature where it stirred for 18 hours. The reaction mixture was concentrated under reduced pressure to a residual oil. The oil was distilled under reduced pressure yielding 30.7 grams of distillate, b.p. 60° C/0.8 mm, that was predominantly S-propyl thiophosphoryl dichloride. The nmr spectrum was consistent with the proposed structure.

Step B

Synthesis of O-ethyl S-propyl thiophosphoryl chloride as an intermediate

A stirred solution of 7.5 grams (0.039 mole) of S-propyl thiophosphoryl dichloride in 40 ml of toluene was cooled to 0° C., and 2.2 grams (0.047 mole) of ethanol was added dropwise. Upon completion of addition, 3.1 grams (0.039 mole) of pyridine was added dropwise. The reaction mixture was allowed to warm to ambient temperature, and then it was placed in a freezer where it stood for 18 hours. The reaction mixture was filtered to collect 7.0 grams of O-ethyl S-propyl thiophosphoryl chloride as a solid. The nmr spectrum was consistent with the proposed structure.

Step C

Synthesis of O-ethyl S-propyl ) O-(12,12-difluoro-11-dodecenyl) thiophosphate

This compound was prepared in a manner analogous to that of Example 12, using 0.99 gram (0.0045 mole) of 12,12-difluoro-11-dodecen-1-ol (prepared in Example 5), 1.0 gram (0.049 mole) of O-ethyl S-propyl thiophosphoryl chloride, 0.45 gram (0.0045 mole) of triethylamine, and a catalytic amount of p-dimethylaminopyridine in 15 ml of methylene chloride. The yield of O-ethyl S-propyl O-(12,12-difluoro-11-dodecenyl)thiophosphate was 0.91 gram. The nmr spectrum was consistent with the proposed structure.

EXAMPLE 23

SYNTHESIS OF 6,6-DIFLUORO-5-HEXEN-1-OL

Compound 22

To a stirred solution of 0.84 gram (0.0121 mole) of sodium hydroxide in 1.5 ml of water was added a solution of 3.3 grams (0.0121 mole) of 6,6-difluoro-5-hexenyl 4-chlorobenzoate (prepared in Example 19) in 20 ml of ethanol. Upon completion of addition, the reaction mixture was warmed to reflux where it was stirred for 18 hours. After this time the reaction mixture was cooled to ambient temperature, and it was concentrated under reduced pressure to a residual semi-solid. The semi-solid was taken up in water and diethyl ether. The aqueous layer was separated, and it was washed with two 100 ml portions of diethyl ether. The ether washes were combined with the organic layer, and the combination was washed in turn with one 50 ml portion of water and one 100 ml portion of an aqueous solution saturated with sodium chloride. The organic layer was dried with magnesium sulfate and filtered. The filtrate was concentrated under reduced pressure yielding 1.6 grams of 6,6-difluoro-5-hexen-1-ol. The nmr spectrum was consistent with the proposed structure.

The fluoroalkane/fluoroalkene derivatives of the present invention were tested for insecticidal and acaricidal activity in foliar and soil evaluations against the beet armyworm (*Spodoptera exigua* (Hubner)), southern armyworm (*Spodoptera eridania*), southern corn rootworm (*Diabrotica undecimpunctata* howardi), Mexican bean beetle (*Epilachna varvestis*), cabbage looper (*Trichoplusia ni*), pea aphid (*Acyrthosiphon pisum*), tobacco budworm (*Heliothis virescens*) and twospotted spider mite (*Tetranychus urticae*).

In initial tests to determine activity against insects and acarids on foliage, 6–10 day old pinto bean (*Phaseolus vuloaris*) or fava bean (*Vicia faba*) plants were sprayed to runoff on both upper and lower leaf surfaces with 10% (v/v) acetone:water solutions of test chemical to provide an application rate of 1000 ppm. The 10% acetone-water solvent used to prepare the solutions of test chemical contained one drop of surfactant per 100 ml of solvent. Two plants were sprayed for each insect species and application rate of test chemical. The sprayed plants were transferred to a hood where they were kept until the spray had dried.

Two pinto bean plants treated with test chemical as described above were removed from their pots by cutting the stem just above the soil line. The excised leaves and stems from each plant were placed in individual 3-ounce paper cups. Ten third instar (10–12 days old) Mexican bean beetle larvae (MBB) or third instar (8–10 days old) southern armyworm larvae (SAW) were counted into each cup, taking care not to cause injury. An opaque plastic lid was placed on each cup, which was then held for a 48 hour exposure period at 26° C. and 50% relative humidity. At the end of the 48 hour exposure period the cups were opened, and the numbers of dead and live insects were counted. Moribund larvae which were disoriented or unable to crawl normally were counted as dead. Using the insect counts, the efficacy of the test chemical was expressed in percent mortality. The condition of the test plant was also observed for phytotoxicity and reduction of feeding damage as compared to an untreated check.

Tests were conducted in a similar manner as described above using first instar (7–8 days old) beet armyworm larvae (BAW). The tests differed in that a 7.5 cm disk of filter paper and 0.5–1.0 ml of distilled water were placed in the bottom of each cup prior to the placement of the excised test plant. The plants were held for a 96 hour exposure period at 26° C. and 50% relative humidity.

Two fava bean plants treated with test chemical as described above were each placed in their entirety, including the pot, into individual 48-ounce waxed paper containers. Ten adult pea aphids (PA) were counted into each container. A plastic dome lid was placed on each container which was then held for a 48-hour exposure period at 26° C. and 50% relative humidity. Efficacy of the test chemical was determined as previously described.

Leaves infested with adult twospotted spider (TSM) mites were removed from culture plants and cut into segments containing 50–75 female mites. Each segment was placed onto the upper leaf surface of a whole pinto bean plant. After the mites had migrated to the under surfaces of the leaves, the leaf segments used to infest were removed and each plant sprayed with test chemical as described above. After the plants had dried, the entire plant and pot were placed in a metal tray in a hood. A supply of water in the tray kept the plants turgid throughout a 48-hour exposure period at 26° C. under constant light.

Activity against twospotted spider mites was estimated by comparing the amount of feeding damage (silvery discoloration of leaf) and webbing on the test plants to the untreated check. Test plants with feeding damage and webbing equal to the check were considered inactive. Test plants that show reduced feeding damage or webbing were examined under a microscope at approximately 10×magnification. Only adult female mites on the underside of the leaf were counted. Percent mortality was calculated by dividing the number of dead mites by the total number of mites on the leaf.

In initial tests to determine activity against insects in the soil, five ml of a 10% acetone/water solution containing the appropriate amount of candidate insecticide was pipetted into 30 grams of air-dried soil in a 3 ounce plastic cup to provide a treated soil containing 10 or 15 ppm of test chemical. The results of these tests are reported in Table II. The treated soil was allowed to stand uncovered in a hood for 30 minutes to evaporate the acetone. The dried, treated soil in each cup was thoroughly mixed and two 3-day old corn sprouts and ten early third stage (9–10 days old) southern corn rootworm larvae (SCR) were placed in each cup. The cups were covered with a plastic lid, placed in a closed plastic bag and then incubated in a holding room at 23°–26° C. for two days. After this time, the unaffected larvae were extracted from the soil and percent mortality determined.

The results of the foregoing tests are shown in Table II.

TABLE II

FOLIAR/SOIL INSECTICIDAL AND ACARICIDAL ACTIVITY*

| Cmpd No | % Kill | | | | | | |
|---|---|---|---|---|---|---|---|
| | BAW | CL | MBB | PA | SAW | SCR** | TSM |
| 001 | | | 0 | 0 | 0 | 60 | |
| 003 | | 0 | 60 | 0 | | 1 | 100 |
| 004 | | | 0 | 0 | 0 | 60 | |
| 005 | 10 | | 0 | 0 | | 10 | |
| 006 | | 0 | 0 | 0 | | 1 | |
| 007 | 15 | | 0 | 0 | | 35 | |

TABLE II-continued

FOLIAR/SOIL INSECTICIDAL AND ACARICIDAL ACTIVITY*

| Cmpd No | BAW | CL | MBB | PA | SAW | SCR** | TSM |
|---|---|---|---|---|---|---|---|
| 008 |  | 0 | 0 | 0 |  | A |  |
| 009 |  |  | 0 | 0 | 0 | 0 |  |
| 010 |  |  | 0 | 0 | 0 | A | 0 |
| 011 |  | 20 | 10 | 95 |  | I | 0 |
| 012 |  |  | 0 | 0 | 0 | I | 0 |
| 013 |  |  | 0 | 0 | 0 | I | 0 |
| 014 |  |  | 95 | 100 | 0 | A | 0 |
| 015 |  |  | 0 | 0 | 0 |  | 0 |
| 016 |  |  | 0 | 0 | 0 | I | 0 |
| 017 |  |  | 0 | 0 | 0 | I | 0 |
| 018 |  |  | 100 | 50 | 0 | I | 0 |
| 019 |  |  | 0 | 0 | 0 | I | 0 |
| 020 | 95 |  | 0 | 0 |  | 30 |  |
| 021 |  | 0 | 0 | 0 |  | I |  |
| 022 |  | 80 | 35 | 100 |  | A | 100 |
| 023 |  | 0 | 0 | 0 |  | I |  |
| 024 |  | 20 | 75 | 100 |  | A |  |
| 025 |  | 30 | 100 | 100 |  | I | 100 |
| 026 |  |  | 5 |  |  |  |  |
| 027 |  | 50 | 35 | 60 |  | I | 100 |
| 028 |  | 0 | 0 | 0 |  | A | 90 |
| 029 |  | 0 | 0 | 0 |  | I |  |
| 030 |  | 15 | 0 | 0 |  | A |  |
| 031 |  |  | 0 | 0 | 0 | 0 |  |
| 032 |  |  | 0 | 0 | 0 | I | 0 |
| 033 |  |  | 0 | 0 | 0 | I | 0 |
| 034 |  |  | 100 | 0 | 0 | A | 0 |
| 035 |  |  | 0 | 0 | 0 | I | 0 |
| 036 |  |  | 0 | 0 | 0 | 60 |  |
| 037 |  |  | 55 | 0 | 0 | A | 0 |
| 038 |  |  | 0 | 0 | 0 | I | 0 |
| 039 |  |  | 55 | 0 | 0 | A | 0 |
| 040 |  |  | 60 | 0 | 0 | A | 0 |
| 041 |  |  | 100 | 0 | 0 | A | 0 |
| 042 |  |  | 0 | 0 | 0 | I | 0 |
| 043 |  |  | 75 | 0 | 0 |  | 0 |
|  |  |  | 45 | 0 | 0 | I |  |
|  |  |  |  |  |  | 70 |  |
| 044 |  |  | 0 | 0 | 0 | I | 0 |
| 045 |  |  | 0 | 0 | 0 | A | 0 |
| 046 |  |  | 0 | 0 | 0 | I | 0 |
| 047 |  |  | 0 | 0 | 0 | I | 0 |
| 048 |  |  | 0 | 0 | 0 |  | 0 |
| 049 |  | 30 | 0 | 0 |  | I | 25 |
| 051 |  | 5 | 40 | 50 |  | I | 100 |
| 052 |  | 5 | 20 | 0 |  | I | 100 |
| 053 |  | 40 | 15 | 0 |  | I | 100 |
| 054 |  |  | 15 | 0 | 0 | A | 0 |
| 055 |  | 15 | 0 | 0 |  | I | 0 |
| 056 |  | 15 | 10 | 5 |  | A | 99 |
| 057 |  | 70 | 95 | 0 |  | I | 100 |
| 058 |  | 10 | 80 | 0 |  | I | 100 |
| 059 |  | 10 | 85 | 0 |  | I | 100 |
| 060 |  | 65 | 90 | 0 |  | I | 100 |
| 061 |  | 45 | 80 | 0 |  | I | 0 |
| 062 |  |  | 0 | 0 | 0 | 60 |  |
| 063 |  | 30 | 60 | 100 |  | I | 100 |
| 064 |  | 15 | 90 | 70 |  | I | 100 |
| 065 |  | 45 | 80 | 100 |  | A | 100 |
| 066 |  | 0 | 95 | 90 |  | A | 85 |
| 067 |  | 50 | 100 | 100 |  | I | 100 |
| 069 |  | 20 | 100 | 100 |  | I | 100 |
| 070 |  | 0 | 0 | 0 |  | I |  |
| 071 | 0 |  | 0 | 0 |  | 100 |  |
| 072 |  |  | 0 | 0 | 0 | A | 0 |
| 073 |  |  | 0 | 0 | 0 | I | 0 |
| 074 |  |  | 0 | 0 | 0 | 65 |  |
| 075 |  | 25 | 0 | 100 |  | I | 100 |
| 076 |  |  | 100 | 100 | 50 | A | 50 |
| 077 |  |  | 5 | 0 |  |  |  |
| 078 |  |  | 100 | 90 | 50 | A | 100 |
| 079 |  |  | 0 | 0 | 0 |  | 0 |
|  |  |  |  |  | 0 | I |  |
| 080 |  |  | 0 | 0 | 0 | I | 0 |
| 081 |  |  | 0 | 0 | 0 | I | 0 |
| 082 |  | 0 | 0 | 0 |  | I |  |
| 083 |  |  | 45 | 95 | 90 | A | 100 |
| 084 |  | 65 | 70 | 95 |  | A | 100 |
| 085 |  | 55 | 85 | 100 |  | A | 100 |
| 086 |  | 40 | 100 | 40 |  | A | 100 |
| 087 |  | 100 | 95 | 100 |  | A | 100 |
| 088 |  | 0 | 20 | 100 |  | A | 100 |
| 089 |  | 80 | 100 | 75 |  | A |  |
| 090 |  | 60 | 100 | 20 |  | I | 100 |
| 091 |  | 60 | 100 | 100 |  | I | 100 |
| 092 |  | 0 | 90 | 100 |  | I | 100 |
| 093 |  | 85 | 100 | 100 |  | I | 100 |
| 094 |  | 0 | 90 | 100 |  | A | 100 |
| 095 |  | 90 | 100 | 100 |  | A | 100 |
| 096 |  | 75 | 50 | 100 |  | I | 100 |
| 097 |  |  | 0 | 0 | 0 | A | 0 |
| 098 |  |  | 0 | 0 | 0 | I | 0 |
| 099 |  | 0 | 0 | 0 |  | I |  |
| 100 |  | 50 | 100 | 85 |  | I | 100 |
| 101 |  | 50 | 100 | 95 |  | A | 100 |
| 102 |  | 60 | 100 | 75 |  | I | 100 |
| 103 |  |  | 100 | 0 | 0 | 100 |  |
| 104 |  | 10 | 5 | 0 |  | I | 0 |
| 105 |  | 15 | 95 | 75 |  | A |  |
| 106 |  | 35 | 95 | 100 |  | I | 100 |
| 107 |  | 60 | 95 | 100 |  | I | 100 |
| 108 |  | 50 | 100 | 100 |  | A | 98 |
| 109 |  | 0 | 70 | 45 |  | A |  |
| 110 |  | 0 | 90 | 50 |  | A |  |
| 111 |  | 30 | 95 | 75 |  | A |  |
| 112 |  | 45 | 100 | 100 |  | I | 100 |
| 113 |  | 60 | 100 | 100 |  | A | 100 |
| 114 |  | 50 | 100 | 100 |  | I | 100 |
| 115 |  |  | 100 | 0 | 0 | 80 |  |
| 116 |  | 70 | 95 | 100 |  | I | 100 |
| 117 |  | 30 | 25 | 90 |  | A | 100 |
| 118 |  | 85 | 100 | 100 |  | A | 100 |
| 119 |  | 60 | 70 | 100 |  | I | 100 |
| 120 |  | 25 | 50 | 100 |  | I | 100 |
| 121 |  | 40 | 20 | 80 |  | A | 100 |
| 122 |  | 40 | 5 | 90 |  | A | 100 |
| 123 |  | 85 | 100 | 95 |  | A | 100 |
| 124 |  | 40 | 20 | 10 |  | A | 100 |
| 125 |  | 35 | 60 | 100 |  | A | 100 |
| 126 |  | 70 | 85 | 100 |  | I | 100 |
| 127 |  | 10 | 100 | 100 |  | A | 100 |
| 128 |  |  | 100 | 0 | 0 | A | 0 |
| 129 | 0 |  | 85 | 0 |  | 0 |  |
| 130 | 0 |  | 100 | 0 |  | 20 |  |
| 131 |  | 10 | 100 | 100 |  | A | 100 |
| 132 |  | 35 | 90 | 100 |  | A | 100 |
| 133 |  | 55 | 95 | 90 |  | A | 100 |
| 134 |  | 75 | 100 | 100 |  | A | 100 |
| 135 | 0 |  | 90 | 75 |  | A |  |
| 136 |  | 0 | 0 | 0 |  | A |  |
| 137 |  | 20 | 0 | 0 |  | I | 100 |
| 138 |  |  | 0 | 0 | 0 | A | 0 |
| 139 | 0 |  | 0 | 0 |  | A |  |
| 140 |  |  | 0 | 0 | 0 | I | 50 |
| 141 |  | 0 | 0 | 70 |  | A |  |
| 142 |  | 0 | 0 | 0 |  | I |  |
| 143 |  | 30 | 100 | 100 |  | A |  |
| 144 |  | 0 | 0 | 0 |  | A |  |
| 145 |  | 80 | 100 | 100 |  | A |  |
| 146 |  | 0 | 0 | 0 |  | I | 75 |
| 147 |  | 95 | 90 | 90 |  | A | 100 |
| 148 |  | 0 | 0 | 0 |  | I |  |
| 149 |  | 70 | 100 | 75 |  | A |  |
| 150 |  |  | 0 | 0 | 0 | I | 0 |
| 151 |  | 0 | 0 | 0 |  | I |  |
| 152 |  | 10 | 90 | 0 |  | I | 100 |
| 153 |  | 25 | 85 | 0 |  | I |  |
| 154 |  | 0 | 75 | 0 |  | A |  |
| 155 |  | 0 | 75 | 0 |  | A |  |
| 156 |  | 60 | 100 | 70 |  | A |  |
| 157 | 100 |  | 90 | 0 |  | I |  |
| 158 | 100 |  | 100 | 0 |  | A |  |
| 159 | 100 |  | 90 | 0 |  | I |  |
| 160 |  | 0 | 95 | 0 |  | I |  |

TABLE II-continued
FOLIAR/SOIL INSECTICIDAL AND ACARICIDAL ACTIVITY*

| Cmpd No | BAW | CL | MBB | PA | SAW | SCR** | TSM |
|---|---|---|---|---|---|---|---|
| 161 | | 0 | 0 | 35 | | A | |
| 162 | | 0 | 70 | 80 | | A | |
| 163 | | 0 | 90 | 80 | | I | |
| 164 | | 0 | 0 | 0 | | I | |
| 165 | | 0 | 0 | 0 | | A | |
| 166 | | 0 | 0 | 0 | | I | |
| 167 | | 0 | 0 | 0 | | I | |
| 168 | | 0 | 0 | 0 | | I | |
| 169 | | 0 | 0 | 70 | | I | |
| 170 | | 0 | 75 | 40 | | I | |
| 171 | | 0 | 40 | 0 | | I | |
| 172 | | ·0 | 0 | 0 | | I | |
| 173 | | 70 | 100 | 100 | | A | 100 |
| 174 | | 70 | 100 | 90 | | A | |
| 175 | | 0 | 100 | 0 | | A | |
| 176 | | 45 | 80 | 90 | | A | |
| 177 | | 0 | 0 | 0 | | I | |
| 178 | 0 | | 95 | 0 | | 0 | |
| 179 | 100 | | 95 | 0 | | I | |
| 180 | 65 | | 95 | 0 | | 55 | |
| 181 | 95 | | 100 | 35 | | 60 | |
| 183 | | 75 | 90 | 0 | | I | |
| 184 | 0 | | 100 | 0 | | I | |
| 185 | 100 | | 100 | 5 | | 25 | |
| 186 | 0 | | 80 | 0 | | 0 | |
| 187 | 5 | | 85 | 0 | | 100 | |
| 188 | | | 100 | 35 | | I | |
| 189 | 100 | | 100 | 0 | | I | |
| 190 | 75 | | 100 | 75 | | 70 | |
| 191 | | 0 | 0 | 0 | | A | |
| 192 | | 20 | 100 | 25 | | I | |
| 193 | 100 | | 100 | 0 | | 45 | |
| 194 | | 50 | 0 | 0 | | I | |
| 195 | | 0 | 70 | 30 | | A | |
| 196 | 100 | | 25 | 0 | | 40 | |
| 197 | | 50 | 100 | 100 | | I | 100 |
| 198 | 0 | | 0 | 10 | | 45 | |
| 199 | | 0 | 0 | 0 | | I | |
| 200 | | 0 | 0 | 35 | | I | |
| 201 | | | 0 | 0 | 0 | A | 0 |
| 202 | | | 100 | 0 | 0 | I | 0 |
| 203 | | | 0 | 0 | 0 | | 0 |
| 204 | | | 0 | 0 | 0 | I | 0 |
| 205 | | | 100 | 90 | 50 | A | 100 |
| 206 | | | 0 | 0 | 0 | I | 0 |
| 207 | | 45 | 100 | 70 | | I | 100 |
| 208 | | 0 | 0 | 0 | 0 | I | 0 |
| 209 | | 40 | 100 | 0 | | I | 100 |
| 210 | | 25 | 85 | 0 | | I | 100 |
| 211 | | 55 | 95 | 0 | | I | 100 |
| 212 | | 25 | 100 | 0 | | A | 100 |
| 213 | | 10 | 90 | 0 | | I | 30 |
| 214 | | 0 | 20 | 60 | | I | 100 |
| 215 | | 55 | 100 | 100 | | I | 100 |
| 216 | | 15 | 0 | 0 | | A | 100 |
| 217 | | 0 | 0 | 0 | | I | 0 |
| 218 | | 0 | 100 | 40 | | A | 100 |
| 219 | | 75 | 0 | 0 | | I | 85 |
| 220 | | 90 | 70 | 0 | | A | 95 |
| 221 | | 20 | 100 | 0 | | I | 0 |

*Exposure time for SCR to the test chemical was either 48 or 72 hours. Exposure time for the other test species was 48 hours. Application Rates: 1000 ppm for BAW, CL, MBB, PA, SAW, TSM; 10 or 15 ppm for SCR.
**A = Activity of 70% or greater; I = Activity of less than 70%.

The compounds of the present invention were tested against the pea aphid for systemic activity. In this test, week-old fava bean plants were each planted in a three ounce pot containing 240 grams of sand. The plants were watered and left at ambient temperature for 24 hours. The plants then were each placed in a 46 ounce paper container. Two plant replicates were provided for each test chemical. Ten ml of a water-acetone solution containing sufficient test chemical to provide an application rate of 50 ppm was poured evenly over the surface of the sand of the potted plant. Care was taken not to wet the foliage or stem of the plant. The plants were allowed to stand for two hours and then 50 ml of water was added to each pot. The plants were placed in a growth chamber for two days to allow the test chemical to become translocated into the plant. After this time approximately 460 grams of fresh sand was added to each pot to avoid direct contact of the treated sand with the test insects. Ten test insects, in the present case pea aphids, were infested to the foliage of each plant. After infestation, each paper container was covered with a 20×20 cm nylon screen which was secured with a rubber band around the container. The infested plants were then placed in a growth chamber programmed at 19° C. for ten hours of light and 14 hours of darkness. Pea aphid mortality and plant phytotoxicity were assessed two days after infestation.

A number of compounds of the present invention were active in the systemic test. The results are shown in Table III.

TABLE III
SYSTEMIC FOLIAR EVALUATION OF THE INSECTICIDAL ACTIVITY

| Cmpd No | Rate (PPM) | % Kill PA* |
|---|---|---|
| 003 | 50 | A |
| 011 | 50 | A |
| 021 | 50 | A |
| 022 | 50 | A |
| 024 | 50 | A |
| 025 | 50 | A |
| 026 | 25 | 70 |
| 056 | 50 | A |
| 059 | 50 | A |
| 063 | 50 | A |
| 064 | 50 | A |
| 065 | 50 | A |
| 066 | 50 | A |
| 067 | 50 | A |
| 069 | 50 | A |
| 075 | 50 | A |
| 077 | 25 | 70 |
| 083 | 50 | A |
| 084 | 50 | A |
| 085 | 50 | A |
| 087 | 50 | A |
| 088 | 50 | A |
| 091 | 50 | A |
| 092 | 50 | A |
| 093 | 50 | A |
| 094 | 50 | A |
| 095 | 50 | A |
| 096 | 50 | A |
| 100 | 50 | A |
| 101 | 50 | A |
| 105 | 50 | A |
| 106 | 50 | A |
| 107 | 50 | A |
| 108 | 50 | A |
| 109 | 50 | A |
| 110 | 50 | A |
| 111 | 50 | A |
| 112 | 50 | A |
| 113 | 50 | A |
| 114 | 50 | A |
| 116 | 50 | A |
| 118 | 50 | A |
| 119 | 50 | A |
| 120 | 50 | A |
| 121 | 50 | A |
| 122 | 50 | A |
| 123 | 50 | A |
| 124 | 50 | A |
| 125 | 50 | A |
| 126 | 50 | A |
| 127 | 50 | A |

TABLE III-continued
SYSTEMIC FOLIAR EVALUATION OF THE INSECTICIDAL ACTIVITY

| Cmpd No | Rate (PPM) | % Kill PA* |
|---|---|---|
| 130 | 25 | 75 |
| 131 | 50 | A |
| 132 | 50 | A |
| 134 | 50 | A |
| 135 | 50 | A |
| 141 | 50 | A |
| 143 | 50 | A |
| 144 | 50 | A |
| 145 | 50 | A |
| 147 | 50 | A |
| 149 | 50 | A |
| 156 | 50 | A |
| 173 | 50 | A |
| 174 | 50 | A |
| 180 | 50 | 100 |
| 181 | 50 | 95 |
| 182 | 50 | 75 |
| 184 | 50 | A |
| 188 | 25 | 100 |
| 190 | 25 | 60 |
| 193 | 50 | 95 |
| 195 | 50 | A |
| 196 | 50 | 5 |
| 197 | 50 | A |
| 198 | 50 | 10 |
| 215 | 50 | A |
| 218 | 50 | A |

*A = 70% kill or greater; insect exposure time is 48 hours

The fluoroalkane/fluoroalkene derivatives of the present invention were tested against the soil-borne root-knot nematode (*Meloidogyne incognita*), the stunt nematode (*Tylenchorhynchus claytoni*), the lesion nematode (*Pratylenchus penetrans*), the soybean cyst nematode (*Heterodera glycines*), and the free-living *Caenorhabditis elegans*.

In tests to determine activity against *C. elegans*, one milliliter of a test medium consisting of 56 mg ampicillin, 10,000 units of mycostatin and 10 ml of a dense suspension of *Escherichia coli* per 100 ml of a buffer solution, was pipetted into each well of a 24-well microtiter plate. The *E. coli* act as the source of food for the *C. elegans* nematode. The candidate nematicides, in the appropriate concentration in dimethylsulfoxide, were added to the wells in 2.5 µl volumes. Each rate of application was replicated two to three times. After thorough mixing of the contents of each well, 50 to 100 µl of a nematode suspension in a buffer was added so that each well received 10–15 nematodes. After the nematodes were added, the microtiter plates were incubated at 20° C. for 5–6 days. The effect of the candidate nematicide on the survival and the reproduction of *C. elegans* was then evaluated by comparison of the level of population development in the treated wells with that in untreated wells. Specific deleterious effects on population development, such as reduced egg hatch or molting disruption, were noted if they were evident.

The results are shown in Table IV.

TABLE IV
INITIAL NEMATICIDAL ACTIVITY AGAINST *C. ELEGANS* NEMATODE
Rate of Application: 5 ppm

| Compound No. | Percent Inhibition of Reproduction | Percent Mortality | Remarks* |
|---|---|---|---|
| 010 | 13 | 0 | |
| 030 | 88 | 0 | MOA |
| 033 | 0 | 0 | |
| 034 | 25 | 0 | |
| 035 | 0 | 0 | |
| 036 | 100 | 0 | MOA |
| 037 | 100 | 100 | |
| 038 | 50 | 0 | MOA |
| 039 | 100 | 88 | |
| 040 | 100 | 38 | |
| 041 | 100 | 13 | |
| 042 | 0 | 0 | |
| 043 | 75 | 0 | MOA |
| 044 | 0 | 0 | |
| 045 | 0 | 0 | |
| 046 | 0 | 0 | |
| 047 | 0 | 0 | |
| 050 | 63 | 0 | |
| 054 | 0 | 0 | |
| 073 | 0 | 0 | |
| 097 | 100 | 0 | MOA |
| 098 | 100 | 0 | MOA |
| 103 | 0 | 0 | |
| 115 | 50 | 0 | |
| 138 | 0 | 0 | |
| 150 | 100 | 0 | MOA |
| 201 | 100 | 100 | |
| 204 | 100 | 100 | |

*MOA — Unusual Mode of Action Noted:
Compound No 30 reduced egg hatch.
Compound No 36 prevented egg hatch.
Compound No 38 reduced egg hatch.
Compound No 43 reduced egg hatch.
Compound No 97 prevented egg hatch.
Compound No 98 prevented egg hatch.
Compound No 150 prevented egg hatch.

In tests to determine activity against the root-knot nematode, the formulated candidate nematicide was incorporated into nematode larvae- and egg-infested soil at rates varying from 10 to 0.312 ppm. A cucumber or tomato seedling was planted in each pot. The tests were evaluated approximately two weeks post-treatment.

In general the compounds of the present invention that were tested against the root-knot nematode provided good to excellent control of this species. Representative results are shown in Table V.

TABLE V
NEMATICIDAL ACTIVITY AGAINST ROOT-KNOT NEMATODE

| Compound No. | Rate (PPM) | Percent Control | Plant Injury* |
|---|---|---|---|
| 008 | 10 | 0 | |
| 010 | 10 | 75 | |
| 012 | 10 | 50 | |
| 013 | 10 | 25 | |
| 014 | 10 | 100 | |
| 016 | 10 | 38 | |
| 018 | 10 | 50 | |
| 019 | 10 | 50 | |
| 026 | 5 | 99 | G1 |
| 030 | 10 | 100 | |
| 032 | 10 | 96 | |
| 033 | 10 | 25 | R2 |
| 034 | 10 | 13 | |
| 035 | 10 | 80 | R3 |
| 036 | 10 | 75 | |
| | 10 | 96 | |
| 037 | 2.5 | 96 | |
| 038 | 10 | 0 | |
| 039 | 10 | 100 | |
| | 10 | 100 | R2 |
| 040 | 5 | 100 | R2 |

TABLE V-continued
NEMATICIDAL ACTIVITY AGAINST ROOT-KNOT NEMATODE

| Compound No. | Rate (PPM) | Percent Control | Plant Injury* |
|---|---|---|---|
| 042 | 10 | 0 | |
| 043 | 10 | 81 | |
|  | 10 | 100 | |
| 044 | 10 | 0 | |
| 045 | 10 | 0 | |
| 046 | 10 | 0 | |
| 047 | 10 | 0 | |
| 062 | 10 | 50 | |
| 072 | 10 | 50 | |
| 073 | 10 | 13 | |
| 076 | 10 | 100 | |
|  | 10 | 100 | R2 |
| 077 | 5 | 86 | |
| 078 | 10 | 80 | |
| 079 | 10 | 0 | |
| 080 | 10 | 0 | |
| 081 | 10 | 0 | |
| 097 | 10 | 99 | R1 |
| 098 | 10 | 97 | R1 |
| 103 | 5 | 68 | R1 |
| 115 | 10 | 99 | |
|  | 10 | 100 | G2 |
| 129 | 5 | 76 | |
| 130 | 5 | 100 | |
| 138 | 10 | 0 | |
| 140 | 10 | 100 | |
| 150 | 10 | 100 | |
| 157 | 5 | 98 | |
| 158 | 5 | 100 | |
| 159 | 5 | 97 | |
| 178 | 5 | 44 | |
| 179 | 5 | 100 | |
|  | 5 | 98 | |
| 180 | 5 | 99 | |
| 181 | 5 | 99 | R1 |
| 182 | 5 | 100 | |
| 184 | 5 | 0 | |
| 185 | 5 | 98 | G2 |
| 186 | 5 | 83 | |
| 187 | 5 | 97 | |
| 188 | 5 | 100 | |
| 189 | 5 | 100 | |
|  | 5 | 98 | |
|  | 5 | 98 | |
| 190 | 5 | 100 | G1 |
| 193 | 5 | 99 | |
| 196 | 5 | 99 | |
| 198 | 5 | 0 | |
| 201 | 10 | 0 | |
| 202 | 10 | 97 | |
| 203 | 10 | 13 | R2 |
|  | 10 | 0 | |
| 204 | 10 | 99 | |
| 205 | 10 | 63 | |
| 208 | 10 | 0 | |

*R and G indicate two types of phytotoxic symptoms:
(R) Injury to root
(G) Reduction in overall plant growth.
The degree of phytotoxic injury is rated as follows:
1 = moderate injury
2 = severe injury
3 = very severe injury In the normal use, the compounds of the present invention usually will not be employed free from admixture or dilution, but ordinarily will be used in a suitable formulated composition compatible with the method of application and comprising a pesticidally effective amount of the compound. The compounds of this invention, like most pesticidal agents, may be blended with the agriculturally acceptable surface-active agents and carriers normally employed for facilitating the dispersion of active ingredients, recognizing the accepted fact that the formulation and mode of application may affect activity. The present compounds may be applied, for example, as sprays, dusts, or granules to the area where pest control is desired, the type of application varying of course with the pest and the environment. Thus, the compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serves as carriers for the compounds. The granule particles are relatively large, a diameter of about 400-2500 microns typically. The particles are either impregnated with the compound from solution or coated with the compound, adhesive sometimes being employed. Granules generally contain 0.05-10%, preferably 0.5-5%, active ingredient as the effective amount.

Dusts are admixtures of the compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the compound. These finely divided solids have an average particle size of less than about 50 microns. A typical dust formulation useful for controlling insects or acarids contains 1 part of the compound, and 99 parts of talc.

The compounds of the present invention may be made into liquid concentrates by dissolution or emulsification in suitable liquids and into solid concentrates by admixture with talc, clays, and other known solid carriers used in the pesticide art. The concentrates are compositions containing, as a pesticidally effective amount, about 5-50% of the present compound and 95-50% inert material, which includes surface-active dispersing, emulsifying, and wetting agents, but even higher concentrations of active ingredient may be employed if desired. The concentrates are diluted with water or other liquids for practical application as sprays, or with additional solid carrier for use as dusts.

A typical 50% wettable powder formulation would consist of 50.0% (wt/wt) of active ingredient, 22.0% attapulgite diluent, 22.0% kaolin diluent, and 6.0% sodium salts of sulfonated Kraft lignin emulsifier.

Typical carriers for sold concentrates (also called wettable powders) include fuller's earth, clays, silicas, and other highly absorbent, readily wetted inorganic diluents. A useful solid concentrate formulation might contain 1.5 parts each of sodium lignosulfonate and sodium lauryl-sulfate as wetting agents, 25 parts of active ingredient, and 72 parts of attapulgite clay.

Manufacturing concentrates are useful for shipping low melting compounds of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

A typical 50 gram per liter emulsifiable concentrate formulation would consist of 5.90% (wt/wt) of active ingredient; as emulsifiers: 1.80% of a blend of the calcium salt of dodecylbenzene sulfonate and a nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.50% of a nonionic paste of polyalkylene glycol ether; and 88.10% refined xylene solvent.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1-15% by weight of the composition.

Other useful formulations include simple solutions of the active ingredient in a solvent in which it is completely soluble at the desired concentration, such as acetone or other organic solvents.

A pesticidally effective amount of the compound in an insecticidal, acaricidal or nematicidal composition diluted for application is normally in the range of about 0.001% to about 8% by weight. Many variations of spraying and dusting compositions known in the art may be used by substituting the compounds of this invention into compositions known or apparent in the art.

The insecticidal or acaricidal compositions of this invention may be formulated with other active ingredients, including other acaricides, nematicides, insecticides, fungicides, plant growth regulators, fertilizers, etc. In using the compositions to control insects, acarids or nematodes, it is only necessary that an insecticidally, acaricidally or nematicidally effective amount of the active compound be applied to the locus where control is desired. Such locus may be the insects or acarids themselves, plants upon which the insects or acarids feed, or the insect or acarid habitat. For control of nematodes and soil borne insect, the locus may be the plant or the soil in which the plant is or is about to be planted. For most applications, an insecticidally, acaricidally or nematicidally effective amount will be about 50 to 750 g per hectare, preferably 150 g to 500 g per hectare.

We claim:

1. A compound of the formula $R-(CH_2)_m-CR^2R^3-OR^1$ in which R is a 1,1-difluoroalkenyl group of 2 to 4 carbon atoms, having one to four additional halogen substituents;

m is an integer in the range of 2 to 11 which produces a carbon chain length for the group $R-(CH_2)_m-CR^2R^3-$ in the range of 4 to 14 carbon atoms;

$R^2$ and $R^3$ are independently hydrogen or methyl;

$R^1$ is $-C(O)R^4$; and $R^4$ is selected from alkenyl of 3 to 9 carbon atoms, alkyl of 1 to 11 carbon atoms trihalomethyl, and ethynyl.

2. The compound of claim 1 in which R is $F_2C=CX$, $F_2XCCH=CH$, $F_2XCXC=CH$, or $F_2XCC(X)_n(H)_{2-n}CH=CH$, in which each X is a halogen atom independently selected from bromo, chloro and fluoro and n is 1 or 2.

3. A compound of claim 1 wherein the term R is selected from the group consisting of $F_2ClCCH=CH-$, $F_3CCH=CH-$, $F_2ClCFClCCH=CH-$, $F_2BrCCH=CH-$ and $F_3CClC=CH-$.

4. A compound of claim 3 wherein R is $F_2ClCCH=CH-$.

5. A compound of claim 1 wherein $R^4$ is $C_1-C_{11}$ linear or branched alkyl, $-CCl_3$, $-CF_3$, $-C\equiv CH$, $-CH=CHCH_3$, $-C(CH_3)=CH_2$, $-CH_2CH=CH_2$, $-CH=C(CH_3)_2$, $-C(CH_3O=CH_2$, $-C(CH_3)=CHCH_3$ or $-CH_2CH(CH_3)C_2H_4CH=C(CH_3)_2$.

6. A compound of claim 4 wherein $R^4$ is $C_1-C_{11}$ linear or branched alkyl, $-CCl_3$, $-CF_3$, $-C\equiv CH$, $-CH=CHCH_3$, $-C(CH_3O=CH_2$, $-CH_2CH=CH_2$, $-CH=C(CH_3)_2$, $-C(CH_3)=CH_2$, $-C(CH_3)=CHCH_3$ or $-CH_2CH(CH_3)C_2H_4CH=C(CH_3)_2$.

7. A compound of claim 6 wherein $R^4$ is $C_1-C_3$ linear or branched alkyl, or trifluoromethyl; $R^2$ and $R^3$ are hydrogen; and m is an even number in the range of 2 to 10.

8. A compound of claim 5 wherein $R^2$ and $R^3$ are hydrogen.

9. A compound of claim 7 wherein $R^4$ is methyl.

* * * * *